ℹ US010363055B2

United States Patent
Beira et al.

(10) Patent No.: US 10,363,055 B2
(45) Date of Patent: Jul. 30, 2019

(54) ARTICULATED HAND-HELD INSTRUMENT

(71) Applicant: DistalMotion SA, Lausanne (CH)

(72) Inventors: Ricardo Daniel Rita Beira, Lausanne (CH); Michael Urs Friedrich, Bern (CH)

(73) Assignee: DistalMotion SA, Epalinges (CH)

( * ) Notice: Subject to any disclaimer, the term of this patent is extended or adjusted under 35 U.S.C. 154(b) by 104 days.

(21) Appl. No.: 15/564,194

(22) PCT Filed: Apr. 11, 2016

(86) PCT No.: PCT/IB2016/000542
§ 371 (c)(1),
(2) Date: Oct. 3, 2017

(87) PCT Pub. No.: WO2016/162751
PCT Pub. Date: Oct. 13, 2016

(65) Prior Publication Data
US 2018/0125519 A1  May 10, 2018

Related U.S. Application Data

(60) Provisional application No. 62/280,736, filed on Jan. 20, 2016, provisional application No. 62/145,454, filed on Apr. 9, 2015.

(51) Int. Cl.
*A61B 17/29* (2006.01)
*A61B 34/00* (2016.01)
(Continued)

(52) U.S. Cl.
CPC .... *A61B 17/2909* (2013.01); *A61B 17/00234* (2013.01); *A61B 17/29* (2013.01);
(Continued)

(58) Field of Classification Search
CPC ...... A61B 2017/291; A61B 2017/2927; A61B 17/2909; A61B 34/71; A61B 17/29;
(Continued)

(56) References Cited

U.S. PATENT DOCUMENTS 2,764,301 A  9/1956 Goertz et al.
2,771,199 A  11/1956 Jelatis
(Continued)

FOREIGN PATENT DOCUMENTS

CN  101584594 A  11/2009
CN  101637402 A  2/2010
(Continued)

OTHER PUBLICATIONS

U.S. Appl. No. 13/878,924, filed May 17, 2013.
(Continued)

*Primary Examiner* — Katherine M Shi
(74) *Attorney, Agent, or Firm* — Foley & Lardner LLP; Christopher C. Bolten; Nicola A. Pisano

(57) ABSTRACT

An articulated hand-held medical instrument is provided. The instrument is primarily intended to be used in minimally invasive surgical procedures. The articulated instrument comprises a master-slave architecture whereby user hand movements on a proximal handle element are replicated on a distal end-effector. The proximal handle comprises a number of handle links joined by handle joints that correspond to a number of end-effector links joined by end-effector joints. The articulated hand-held medical instrument can be used in standard laparoscopic procedures in various port arrangements and through the use of standard equipment such as trocars, and movements inside the patient's body may be tracked using available endoscopic cameras.

20 Claims, 43 Drawing Sheets

(51) Int. Cl.
*A61B 17/00* (2006.01)
*A61B 90/00* (2016.01)

(52) U.S. Cl.
CPC ...... *A61B 34/71* (2016.02); *A61B 2017/0046* (2013.01); *A61B 2017/00424* (2013.01); *A61B 2017/00738* (2013.01); *A61B 2017/291* (2013.01); *A61B 2017/2927* (2013.01); *A61B 2017/2929* (2013.01); *A61B 2017/2948* (2013.01); *A61B 2090/0813* (2016.02)

(58) Field of Classification Search
CPC .............. A61B 34/70; A61B 17/00234; A61B 2017/00424; A61B 2017/00738; A61B 34/25; A61B 34/37; A61B 34/77; A61B 90/50; B25J 13/02; B25J 3/02
USPC ............................................ 606/1, 130, 205
See application file for complete search history.

(56) References Cited

U.S. PATENT DOCUMENTS

| | | |
|---|---|---|
| 2,774,488 A | 12/1956 | Goertz |
| 2,846,084 A | 8/1958 | Goertz et al. |
| 3,065,863 A | 11/1962 | Saunders, Jr. |
| 3,095,096 A | 6/1963 | Chesley |
| 3,212,651 A | 10/1965 | Specht et al. |
| 3,261,480 A | 7/1966 | Haaker et al. |
| 3,297,172 A | 1/1967 | Haaker et al. |
| 3,391,801 A | 7/1968 | Haaker |
| 3,425,569 A | 2/1969 | Haaker |
| 4,221,516 A | 9/1980 | Haaker et al. |
| 4,756,655 A | 7/1988 | Jameson |
| 5,147,357 A | 9/1992 | Rose et al. |
| 5,176,352 A | 1/1993 | Braun |
| 5,207,114 A | 5/1993 | Salisbury et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,599,151 A | 2/1997 | Daum et al. |
| 5,603,723 A | 2/1997 | Aranyi et al. |
| 5,631,973 A | 5/1997 | Green |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,784,542 A | 7/1998 | Ohm et al. |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,908,436 A | 6/1999 | Cuschieri et al. |
| 5,951,587 A | 9/1999 | Qureshi et al. |
| 5,976,122 A | 11/1999 | Madhani et al. |
| 6,026,701 A | 2/2000 | Reboulet |
| 6,132,368 A | 10/2000 | Cooper |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,312,435 B1 | 11/2001 | Wallace et al. |
| 6,331,181 B1 | 12/2001 | Tierney et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,394,998 B1 | 5/2002 | Wallace et al. |
| 6,435,794 B1 | 8/2002 | Springer |
| 6,459,926 B1 | 10/2002 | Nowlin et al. |
| 6,491,701 B2 | 12/2002 | Tierney et al. |
| 6,554,844 B2 | 4/2003 | Lee et al. |
| 6,587,750 B2 | 7/2003 | Gerbi et al. |
| 6,594,552 B1 | 7/2003 | Nowlin et al. |
| 6,671,581 B2 | 12/2003 | Niemeyer et al. |
| 6,699,177 B1 | 3/2004 | Wang et al. |
| 6,786,896 B1 | 9/2004 | Madhani et al. |
| 6,788,999 B2 | 9/2004 | Green |
| 6,840,938 B1 | 1/2005 | Morley et al. |
| 6,850,817 B1 | 2/2005 | Green |
| 6,852,107 B2 | 2/2005 | Wang et al. |
| 6,879,880 B2 | 4/2005 | Nowlin et al. |
| 6,902,560 B1 | 6/2005 | Morley et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,048,745 B2 | 5/2006 | Tierney et al. |
| 7,083,571 B2 | 8/2006 | Wang et al. |
| 7,090,637 B2 | 8/2006 | Danitz et al. |
| 7,101,363 B2 | 9/2006 | Nishizawa et al. |
| 7,204,836 B2 | 4/2007 | Wagner et al. |
| 7,232,440 B2 | 6/2007 | Dumbauld et al. |
| 7,306,597 B2 | 12/2007 | Manzo |
| 7,316,681 B2 | 1/2008 | Madhani et al. |
| 7,338,513 B2 | 3/2008 | Lee et al. |
| 7,364,582 B2 | 4/2008 | Lee |
| 7,373,219 B2 | 5/2008 | Nowlin et al. |
| 7,398,707 B2 | 7/2008 | Morley et al. |
| 7,481,824 B2 | 1/2009 | Boudreaux et al. |
| 7,594,912 B2 | 9/2009 | Cooper et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,890,211 B2 | 2/2011 | Green |
| 7,914,521 B2 | 3/2011 | Wang et al. |
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,287,469 B2 | 10/2012 | Stefanchik et al. |
| 8,292,889 B2 | 10/2012 | Cunningham et al. |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,403,832 B2 | 3/2013 | Cunningham et al. |
| 8,418,904 B2 | 4/2013 | Wenchell et al. |
| 8,423,186 B2 | 4/2013 | Itkowitz et al. |
| 8,496,152 B2 | 7/2013 | Viola |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,603,077 B2 | 12/2013 | Cooper et al. |
| 8,617,203 B2 | 12/2013 | Stefanchik et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |

(56) References Cited

U.S. PATENT DOCUMENTS

| | | |
|---|---|---|
| 8,821,480 B2 | 9/2014 | Burbank |
| 8,828,046 B2 | 9/2014 | Stefanchik et al. |
| 8,845,517 B2 | 9/2014 | Russo |
| 8,845,622 B2 | 9/2014 | Paik et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,861 B2 | 8/2015 | Martin et al. |
| 9,149,339 B2 | 10/2015 | Unsworth |
| 9,307,894 B2 | 4/2016 | Von Grunberg et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,696,700 B2 | 7/2017 | Beira et al. |
| 10,071,488 B2 | 9/2018 | Robinson et al. |
| 10,092,359 B2 | 10/2018 | Beira et al. |
| 10,265,129 B2 | 4/2019 | Beira |
| 2002/0040217 A1 | 4/2002 | Jinno |
| 2002/0049367 A1 | 4/2002 | Irion et al. |
| 2002/0072736 A1 | 6/2002 | Tierney et al. |
| 2003/0155747 A1 | 8/2003 | Bridges |
| 2003/0208186 A1 | 11/2003 | Moreyra |
| 2004/0049205 A1 | 3/2004 | Lee et al. |
| 2004/0116906 A1 | 6/2004 | Lipow |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0314181 A1 | 12/2008 | Schena |
| 2009/0036902 A1 | 2/2009 | Dimaio et al. |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0299141 A1 | 12/2009 | Downey et al. |
| 2010/0004508 A1 | 1/2010 | Naito et al. |
| 2010/0011900 A1 | 1/2010 | Burbank |
| 2010/0023025 A1 | 1/2010 | Zeiner et al. |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0331859 A1 | 12/2010 | Omori |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0245643 A1 | 9/2013 | Woodard et al. |
| 2013/0245647 A1 | 9/2013 | Martin et al. |
| 2013/0282027 A1 | 10/2013 | Woodard et al. |
| 2013/0303408 A1 | 11/2013 | Indermuhle |
| 2013/0304083 A1 | 11/2013 | Kaercher et al. |
| 2013/0304084 A1 | 11/2013 | Epfl |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0076088 A1 | 3/2014 | Berkelman et al. |
| 2014/0114481 A1 | 4/2014 | Ogawa et al. |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0195010 A1 | 7/2014 | Epfl |
| 2014/0200561 A1 | 7/2014 | Ingmanson et al. |
| 2014/0207150 A1 | 7/2014 | Rosa et al. |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Markt |
| 2015/0142018 A1 | 5/2015 | Sniffin et al. |
| 2015/0150575 A1 | 6/2015 | Hartoumbekis et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0346053 A1 | 12/2016 | Beira |
| 2016/0374766 A1 | 12/2016 | Schuh |
| 2017/0245954 A1 | 8/2017 | Beira |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |

(56) References Cited

U.S. PATENT DOCUMENTS

| | | |
|---|---|---|
| 2018/0000544 A1 | 1/2018 | Beira |
| 2018/0000550 A1 | 1/2018 | Beira |
| 2018/0055583 A1 | 3/2018 | Schuh et al. |
| 2018/0125519 A1 | 5/2018 | Beira et al. |
| 2018/0125592 A1 | 5/2018 | Beira |
| 2018/0242991 A1 | 8/2018 | Beira |
| 2018/0353252 A1 | 12/2018 | Chassot et al. |

FOREIGN PATENT DOCUMENTS

| | | |
|---|---|---|
| CN | 101732093 A | 6/2010 |
| CN | 103717355 A | 4/2014 |
| DE | 43 03 311 A1 | 8/1994 |
| DE | 19652792 C2 | 5/1999 |
| DE | 10314827 B3 | 4/2004 |
| DE | 10314828 B3 | 7/2004 |
| DE | 10 2012 222 755 | 6/2014 |
| DE | 10 2014 205 036 A1 | 9/2015 |
| DE | 10 2014 205 159 A1 | 9/2015 |
| EP | 0 595 291 A1 | 5/1994 |
| EP | 0 621 009 A1 | 10/1994 |
| EP | 0 677 275 A2 | 10/1995 |
| EP | 0 776 739 A2 | 6/1997 |
| EP | 1 254 642 A1 | 11/2002 |
| EP | 1 279 371 B1 | 12/2004 |
| EP | 1 886 630 A2 | 2/2008 |
| EP | 1 889 579 A2 | 2/2008 |
| EP | 2 058 090 A2 | 5/2009 |
| EP | 1 977 677 B1 | 8/2009 |
| EP | 2 095 778 A1 | 9/2009 |
| EP | 1 889 583 B1 | 4/2011 |
| EP | 2 377 477 B1 | 5/2012 |
| EP | 2 473 119 A2 | 7/2012 |
| EP | 2 305 144 B1 | 10/2012 |
| EP | 2 044 893 B1 | 7/2013 |
| EP | 2 653 110 A1 | 10/2013 |
| EP | 2 679 192 A2 | 1/2014 |
| EP | 2 736 680 A2 | 6/2014 |
| EP | 2 777 561 A1 | 9/2014 |
| EP | 2 783 643 A1 | 10/2014 |
| EP | 2 837 340 A1 | 2/2015 |
| EP | 2 837 354 A1 | 2/2015 |
| EP | 2 554 131 B1 | 8/2015 |
| EP | 2 979 657 A1 | 2/2016 |
| GB | 0 969 899 A | 9/1964 |
| JP | 2004-041580 A | 2/2004 |
| JP | 2007-290096 A | 11/2007 |
| JP | 2008-104620 A | 5/2008 |
| JP | 2009-018027 A | 1/2009 |
| KR | 20110032444 A | 3/2011 |
| KR | 20130031403 A | 3/2013 |
| WO | WO-82/00611 A1 | 3/1982 |
| WO | WO-97/43942 A1 | 11/1997 |
| WO | WO-98/25666 A1 | 6/1998 |
| WO | WO-03/067341 A2 | 8/2003 |
| WO | WO-03/086219 A2 | 10/2003 |
| WO | WO-2004/052171 A2 | 6/2004 |
| WO | WO-2005/009482 A2 | 2/2005 |
| WO | WO-2005/046500 A1 | 5/2005 |
| WO | WO-2006/086663 A2 | 4/2006 |
| WO | WO-2007/133065 A1 | 11/2007 |
| WO | WO-2008/130235 A2 | 10/2008 |
| WO | WO-2009/091497 A2 | 7/2009 |
| WO | WO-2009/095893 A2 | 8/2009 |
| WO | WO-2009/145572 A2 | 12/2009 |
| WO | WO-2009/157719 A2 | 12/2009 |
| WO | WO-2010/019001 A2 | 2/2010 |
| WO | WO-2010/030114 A2 | 3/2010 |
| WO | WO-2010/050771 A2 | 5/2010 |
| WO | WO-2010/083480 A2 | 7/2010 |
| WO | WO-2010/096580 A1 | 8/2010 |
| WO | WO-2010/130817 A1 | 11/2010 |
| WO | WO-2011/027183 A2 | 3/2011 |
| WO | WO-2011/123669 A1 | 10/2011 |
| WO | WO-2012/020386 A1 | 2/2012 |
| WO | WO-2012/049623 A1 | 4/2012 |
| WO | WO-2013/007784 A1 | 1/2013 |
| WO | WO-2013/014621 A1 | 1/2013 |
| WO | WO-2013/014621 A2 | 1/2013 |
| WO | WO-2014/012780 A1 | 1/2014 |
| WO | WO-2014/018447 A1 | 1/2014 |
| WO | WO-2014/067804 A1 | 5/2014 |
| WO | WO-2014/094716 A1 | 6/2014 |
| WO | WO-2014/094717 A1 | 6/2014 |
| WO | WO-2014/094718 A1 | 6/2014 |
| WO | WO-2014/094719 A1 | 6/2014 |
| WO | WO-2014/145148 A2 | 9/2014 |
| WO | WO-2014/156221 A1 | 10/2014 |
| WO | WO-2014/201010 A1 | 12/2014 |
| WO | WO-2014/201538 A1 | 12/2014 |
| WO | WO-2015/081946 A1 | 6/2015 |
| WO | WO-2015/081947 A1 | 6/2015 |
| WO | WO-2015/088647 A1 | 6/2015 |
| WO | WO-2015/088655 A1 | 6/2015 |
| WO | WO-2015/111475 A1 | 7/2015 |
| WO | WO-2015/113933 A1 | 8/2015 |
| WO | WO-2015/129383 A1 | 8/2015 |
| WO | WO-2015/139674 A1 | 9/2015 |
| WO | WO-2015/175200 A1 | 11/2015 |
| WO | WO-2016/030767 A9 | 3/2016 |
| WO | WO-2016/083189 A1 | 6/2016 |
| WO | WO-2016/097861 A1 | 6/2016 |
| WO | WO-2016/097864 A2 | 6/2016 |
| WO | WO-2016/097868 A1 | 6/2016 |
| WO | WO-2016/097871 A1 | 6/2016 |
| WO | WO-2016/097873 A2 | 6/2016 |
| WO | WO-2016/162751 A1 | 10/2016 |
| WO | WO-2016/162752 A1 | 10/2016 |
| WO | WO-2016/183054 A1 | 11/2016 |
| WO | WO-01/6189284 A1 | 12/2016 |
| WO | WO-2016/189284 A1 | 12/2016 |
| WO | WO-2017/015599 A1 | 1/2017 |
| WO | WO-2017/064301 A1 | 4/2017 |
| WO | WO-2017/064303 A1 | 4/2017 |
| WO | WO-2017/064305 A1 | 4/2017 |
| WO | WO-2017/064306 A1 | 4/2017 |

OTHER PUBLICATIONS

U.S. Appl. No. 14/233,184 / U.S. Pat. No. 9,696,700, filed Jan. 16, 2014 / Jul. 4, 2017.
U.S. Appl. No. 15/116,509, filed Aug. 3, 2016.
U.S. Appl. No. 15/506,659, filed Feb. 24, 2017.
U.S. Appl. No. 15/536,539, filed Jun. 15, 2017.
U.S. Appl. No. 15/536,562, filed Jun. 15, 2017.
U.S. Appl. No. 15/536,568, filed Jun. 15, 2017.
U.S. Appl. No. 15/536,573, filed Jun. 15, 2017.
U.S. Appl. No. 15/536,576, filed Jun. 15, 2017.
U.S. Appl. No. 15/564,193, filed Oct. 3, 2017.
U.S. Appl. No. 15/633,611, filed Jun. 26, 2017.
International Search Report & Written Opinion dated Jul. 10, 2018 in Int'l PCT Patent Appl. Serial No. PCT/IB2018/053272.
Abbott, et al., "Design of an Endoluminal NOTES Robotic System," IEEE/RSJ International Conference on Intelligent Robots and Systems, San Diego, CA, pp. 410-416 (2007).
Aesculap Surgical Technologies, Aesculap® Caiman®, Advanced Bipolar Seal and Cut Technology Brochure, 6 pages (retrieved Aug. 31, 2015).
Arata, et al., "Development of a dexterous minimally-invasive surgical system with augmented force feedback capability," IEEE/RSJ International Conference on Intelligent Robots and Systems, pp. 3207-3212 (2005).
Çavuşoğlu, et al., "Laparoscopic Telesurgical Workstation," IEEE Transactions on Robotics and Automation,(15)4:728-739 (1999).
Charles, et al., Dexterity-enhanced Telerobotic Microsurgery, Advanced Robotics, ICAR '97. Proceedings, 8th Int'l Conference (1997).
Dachs, et al., "Novel Surgical Robot Design: Minimizing the Operating Envelope Within the Sterile Field," 28th International Conference, IEEE Engineering in Medicine Biology Society, New York, pp. 1505-1508 (2006).

(56) References Cited

OTHER PUBLICATIONS

Dario, et al., "Novel Mechatronic Tool for Computer-Assisted Arthroscopy," IEEE Transactions on Information Technology in Biomedicine, 4(1):15-29 (Mar. 2000).
Focacci, et al., "Lightweight Hand-held Robot for Laparoscopic Surgery," IEEE International Conference on Robotics & Automation, Rome, Italy, pp. 599-604 (2007).
Guthart, et al., "The Intuitive™ Telesurgery System: Overview and Application," IEEE International Conference on Robotics & Automation, San Francisco, CA, pp. 618-621 (2000).
Ikuta, et al., "Development of Remote Microsurgery Robot and New Surgical Procedure for Deep and Narrow Space," IEEE International Conference on Robotics & Automation, Taipei, Taiwan, pp. 1103-1108 (2003).
Ikuta, et al., "Hyper Redundant Miniature Manipulator 'Hyper Finger' for Remote Minimally Invasive Surgery in Deep Area," IEEE International Conference on Robotics & Automation, Taipei, Taiwan, pp. 1098-1102 (2003).
International Search Report & Written Opinion dated Feb. 2, 2017 in Int'l PCT Patent Appl. Serial No. PCT/IB2016/001286.
International Search Report & Written Opinion dated Jan. 18, 2013 in Int'l PCT Patent Appl Serial No. PCT/IB2012/053786.
International Search Report dated Jan. 18, 2013 in Int'l PCT Patent Appl Serial No. PCT/IB2012/053786.
International Search Report dated Mar. 23, 2012 in Int'l PCT Patent Appl Serial No. PCT/IB2011/054476.
Ishii, et al., "Development of a New Bending Mechanism and Its Application to Robotic Forceps Manipulator," IEEE International Conference on Robotics & Automation, Rome, Italy, pp. 238-243 (2007).
International Search Report & Written Opinion dated Feb. 17, 2016 in Int'l PCT Patent Appl Serial No. PCT/IB2015/002095.
International Search Report & Written Opinion dated May 23, 2016 in Int'l PCT Patent Appl Serial No. PCT/IB2015/002524.
International Search Report & Written Opinion dated Mar. 23, 2012 in Int'l PCT Patent Appl Serial No. PCT/IB2011/054476.
International Search Report & Written Opinion dated Mar. 30, 2015 in Int'l PCT Patent Appl Serial No. PCT/EP2015/051473.
International Search Report & Written Opinion dated Apr. 26, 2016 in Int'l PCT Patent Appl Serial No. PCT/IB2015/002512.
International Search Report & Written Opinion dated May 24, 2016 in Int'l PCT Patent Appl Serial No. PCT/IB2015/002487.
International Search Report & Written Opinion dated Jun. 10, 2016 in Int'l PCT Patent Appl Serial No. PCT/IB2015/002533.
International Search Report & Written Opinion dated Jun. 13, 2016 in Int'l PCT Patent Appl Serial No. PCT/IB2015/002493.
International Search Report & Written Opinion dated Aug. 25, 2016 in Int'l PCT Patent Appl Serial No. PCT/IB2015/000542.
International Search Report & Written Opinion dated Sep. 2, 2016 in Int'l PCT Patent Appl Serial No. PCT/IB2016/000543.
Kobayashi, et al., "Small Occupancy Robotic Mechanisms for Endoscopic Surgery," International Conference on Medical Image Computing and Computer assisted Interventions, pp. 75-82 (2002).
Lang, et al., Intra-operative robotics: NeuroArm., Acta Neurochir Suppl, 109:231-236 (2011).
Mayer, et al., "The Endo[PA]R System for Minimally Invasive Robotic Surgery," IEEE/RSJ International Conference on Intelligent Robots and Systems, Sendai, Japan, pp. 3637-3642 (2004).
Mitsuishi, et al., "Development of a Remote Minimally Invasive Surgical System with Operational Environment Transmission Capability," IEEE International Conference on Robotics & Automation, Taipei, Taiwan, pp. 2663-2670 (2003).
Mitsuishi, et al., Master-slave robotic platform and its feasibility study for micro-neurosurgery, Int. J. Med. Robot., 9(2):180-9 (2013).
Morita, et al., Microsurgical robotic system for the deep surgical field: development of a prototype and feasibility studies in animal and cadaveric models, J. Neurosurg., 103(2):320-7 (2005).
Nakamura, et al., "Multi-DOF Forceps Manipulator System for Laparoscopic Surgery-Mechanism miniaturized & Evaluation of New Interface," 4th International Conference on Medical Image Computing and Computer assisted Interventions (MICCAI2001), pp. 606-613 (2001).
Peirs, et al., "Design of an advanced tool guiding system for robotic surgery," IEEE International Conference on Robotics & Automation, Taipei, Taiwan, pp. 2651-2656 (2003).
Sallé, et al., "Optimal Design of High Dexterity Modular MIS Instrument for Coronary Artery Bypass Grafting," IEEE International Conference on Robotics & Automation, New Orleans, LA, pp. 1276-1281 (2004).
Seibold, et al., "Prototype of Instrument for Minimally Invasive Surgery with 6-Axis Force Sensing Capability," IEEE International Conference on Robotics & Automation, Barcelona, Spain, pp. 496-501 (2005).
Simaan et al., "Dexterous System for Laryngeal Surgery: Multi-Backbone Bending Snake-like Slaves for Teleoperated Dexterous Surgical Tool Manipulation," IEEE International Conference on Robotics & Automation, New Orleans, LA, pp. 351-357 (2004).
Stryker®, Endoscopy, Take a Look Around, Ideal Eyes™ FFD122 HD, Articulating Laparoscope Brochure, 2 pages (2009).
Swiss Search Report dated Jun. 4, 2012 in Swiss Patent Application No. CH 00702/12.
Tavakoli, et al., "Force Reflective Master-Slave System for Minimally Invasive Surgery," IEEE/RSJ International Conference on Intelligent Robots and Systems, Las Vegas, NV, pp. 3077-3082 (2003).
Taylor, et al., "Steady-Hand Robotic System for Microsurgical Augmentation," The International Journal of Robotics Research, 18(12):1201-1210 (1999).
www.cttc.co/technologies/maestro-non-robotic-dexterous-laproscopic-instrument-writs-providing-seven-degrees, "Maestro: Non-Robotic Dexterous Laproscopic Instrument With a Wrist Providing Seven Degrees of Freedom", accessed Nov. 12, 2015, 4 pages.
Yamashita, et al., "Development of Endoscopic Forceps Manipulator Using Multi-Slider Linkage Mechanisms," The 1st Asian Symposium on Computer Aided Surgery-Robotic and Image-Guided Surgery, Ibaraki, Japan, 4 pages (2005).
Zeus, "Robotic Surgical System" available at http://allaboutroboticsurgery.com/zeusrobot.html.

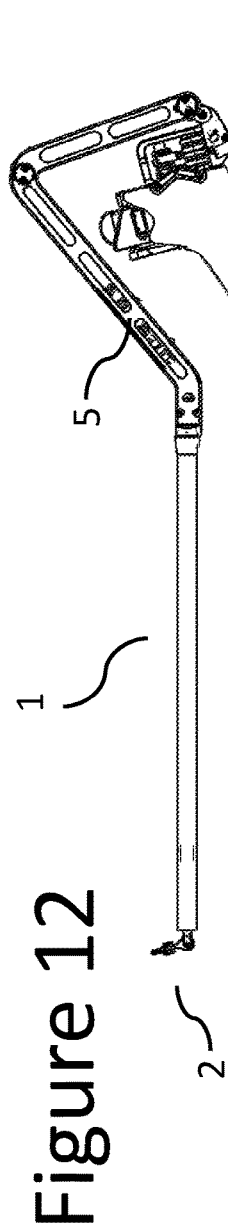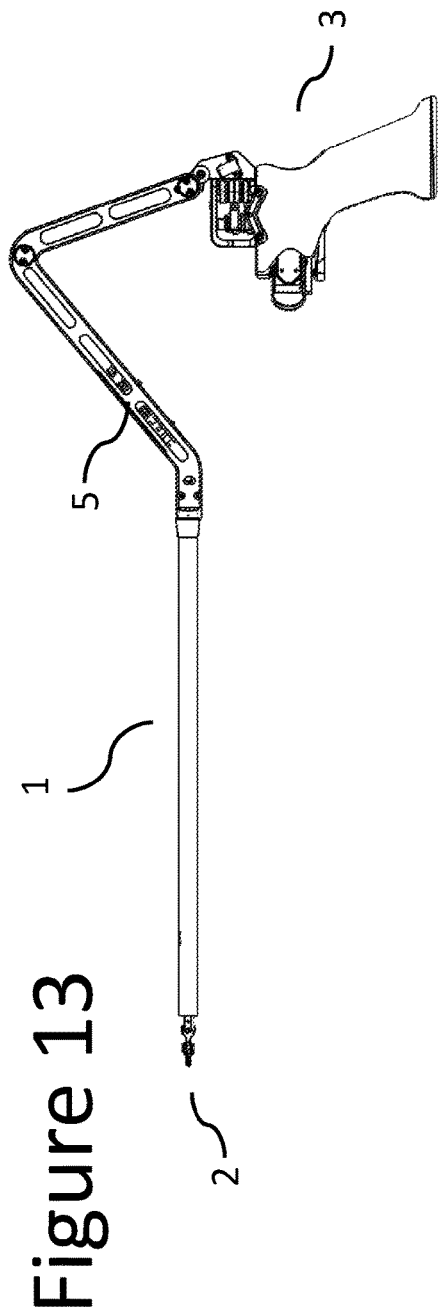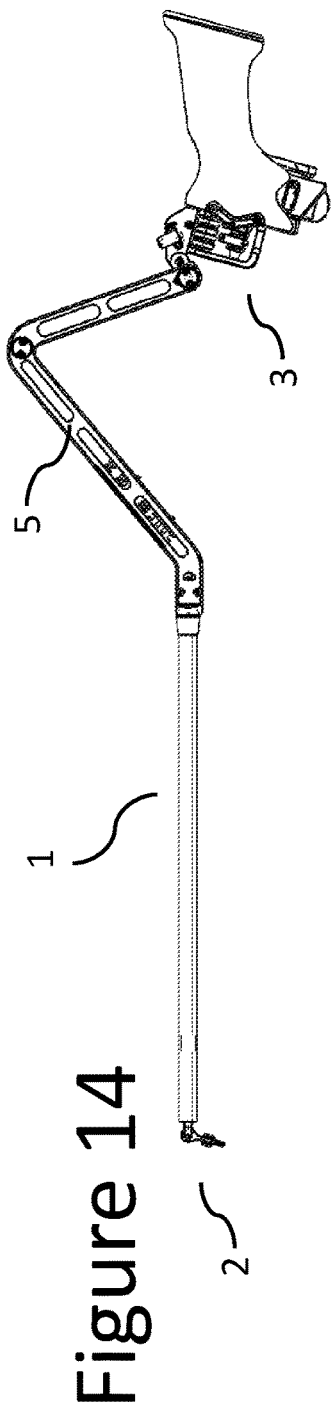

ARTICULATED HAND-HELD INSTRUMENT

CROSS-REFERENCE TO RELATED APPLICATIONS

This application is a national phase of International PCT Patent Application No. PCT/IB2016/000542, filed Apr. 11, 2016, which claims priority to U.S. Provisional Patent Application Nos. 62/280,736, filed Jan. 20, 2016, and 62/145,454, filed Apr. 9, 2015, the entire contents of each of which are incorporated herein by reference.

FIELD OF THE INVENTION

The present invention relates to the field of remotely actuated mechanical systems, more particularly to surgical instruments, and most particularly to articulated hand-held surgical instruments. More specifically, this invention relates to articulated hand-held surgical instruments primarily designed to be used in minimally invasive surgical procedures. The inventive surgical instruments are designed to be used in a full range of minimally invasive surgical procedures and with standard equipment, such as trocars and endoscopic cameras. The articulated hand-held surgical instruments are designed to provide greater reach, range of motion and dexterity than that accessible with the use of standard laparoscopic instruments.

BACKGROUND OF THE INVENTION

Open surgery is still the standard technique for most surgical procedures. It has been used by the medical community for several decades and consists of performing the surgical tasks through a long incision in the abdomen, through which traditional surgical tools are inserted. However, due to the long incision, this approach is extremely invasive for the patients, resulting in substantial blood loss during the surgery and long and painful recovery periods at the hospital.

In order to reduce the invasiveness of open surgery, laparoscopy, a minimally invasive technique, was developed. Instead of a single long incision, four to five small incisions are made in the patient through which appropriately sized surgical instruments and endoscopic cameras are inserted. Because of the low invasiveness, this technique reduces blood loss and shortens hospital stays and pain. When performed by experienced surgeons, this technique can attain clinical outcomes similar to open surgery. However, despite the above-mentioned advantages, laparoscopy requires extremely advanced surgical skills to manipulate the rigid and long instrumentation. The entry incision acts as a point of rotation, decreasing the surgeon's freedom for positioning and orientating the instruments inside the patient. The movements of the surgeon's hand about this incision are inverted and scaled-up relative to the instrument tip ("fulcrum effect"), which removes dexterity, sensibility and magnifies the tremors of the surgeon's hands. In addition, these long and straight instruments force surgeons to work in a uncomfortable posture, which can be tremendously tiring during several hours of operation and result in stress and discomfort for hands, arms and body. Therefore, due to these drawbacks of laparoscopic instrumentation, these minimally invasive techniques are mainly limited to use in simple surgeries, while only a small minority of surgeons is able to use them in complex procedures.

To overcome these limitations, surgical robotic systems were developed to provide an easier-to-use approach to complex minimally invasive surgeries. By means of a computerized robotic interface, these systems enable the performance of remote laparoscopy wherein the surgeon sits at a console manipulating two master manipulators to perform the operation through several small incisions. Like laparoscopy, the robotic approach is also minimally invasive, bringing several advantages over open surgery in terms of pain, blood loss, and recovery time. In addition, it also offers better ergonomy for the surgeon compared to open and laparoscopic techniques. However, although being technically easier, robotic surgery brings several negative aspects. A major disadvantage of these systems is related to the extremely high complexity of existing robotic devices, which are composed of complex mechanical and electronic systems, leading to huge costs of acquisition and maintenance, which are not affordable for the majority of surgical departments worldwide. Another drawback of these systems comes from the fact that current surgical robots are very large, competing for precious space within the operating room environment and significantly increasing preparation time. Access to the patient is thus impaired, which, together with a lack of force-feedback, raises safety concerns.

In addition to robotic systems, several hand-held laparoscopic instruments are known. These instruments provide access to the surgical field without the need for an expensive and cumbersome robotic system, but they often provide poor ergonomy to the user.

There are known examples of hand-held, articulated surgical instruments. However, they present significant drawbacks in their designs. For example, one known articulated instrument (ref) must be attached to the user's forearm by a frame, making its use cumbersome and likely tiring, given that every movement must involve the user moving his entire forearm, which needs to be geometrically aligned with the instrument's shaft. Other known articulated instruments (refs) require the manipulation of knobs or similar elements on the device handle to produce corresponding movements in an end-effector. Such arrangement does not allow for a natural replication of user hand movements.

Accordingly, an aim of the present invention is to provide an articulated hand-held medical instrument that allows for a natural replication of user hand movements on the instrument handle at an end effector. The instrument is to allow for good ergonomy and ease of use as compared to known hand-held articulated instruments.

SUMMARY OF THE INVENTION

Theses aims and other advantages are achieved by a new articulated hand-held medical instrument. The articulated hand-held medical instrument of the present invention is primarily intended to be used in minimally invasive surgical procedures.

The articulated hand-held medical instrument comprises a frame, a proximal handle and a distal end-effector. The proximal handle is joined to the distal end-effector by an instrument tube and a structural frame. The instrument tube may optionally be introduced to the patient's body during a minimally invasive surgical procedure through a trocar or other standard piece of equipment.

The proximal handle of the articulated hand-held surgical instrument is made up of a series of handle links connected by handle joints. The distal end-effector element is generally made up of a number of end-effector links connected by end-effector joints. Mechanical transmission means transmit user motions performed on the proximal handle to the distal end-effector. In this way, the articulated hand-held surgical instrument has a master-slave architecture allowing for the replication of user hand movements on the proximal handle at the distal end-effector. Taken in conjunction with the multiple links and degrees of freedom, this architecture allows for greater dexterity and ergonomy than that accessible with standard laparoscopic instruments.

BRIEF DESCRIPTION OF FIGURES

The invention will be better understood according to the following detailed description of several embodiments with reference to the attached drawings, in which:

FIG. 12 shows the articulated instrument according to an embodiment of the present invention in a first active position;

FIG. 13 shows the articulated instrument according to an embodiment of the present invention in a second active position;

FIG. 14 shows the articulated instrument according to an embodiment of the present invention in a third active position;

DETAILED DESCRIPTION OF THE INVENTION

Figure 1:
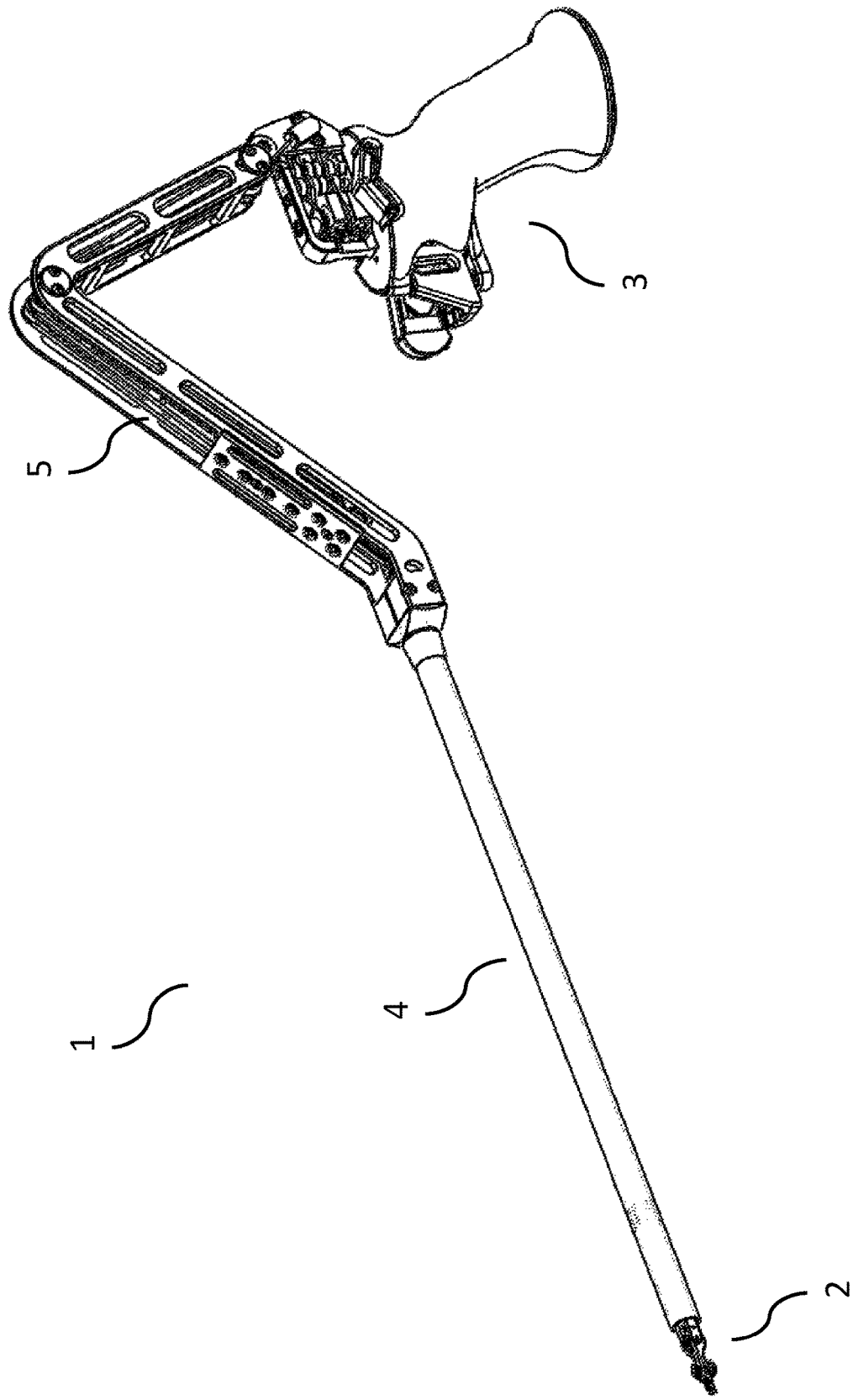
FIG. 1 shows a perspective view of the articulated instrument according to an embodiment of the present invention.

The articulated instrument 1 of FIG. 1, according to an embodiment of the present invention, is intended to be used in minimally invasive surgical procedures.

One of the key features of this type of articulated instrument 1 lies in its master-slave architecture, which enables the replication of the user hand movements, on a proximal handle 3 (the master), by a distal end-effector 2 (the slave) inside the patient's body.

Figure 2:
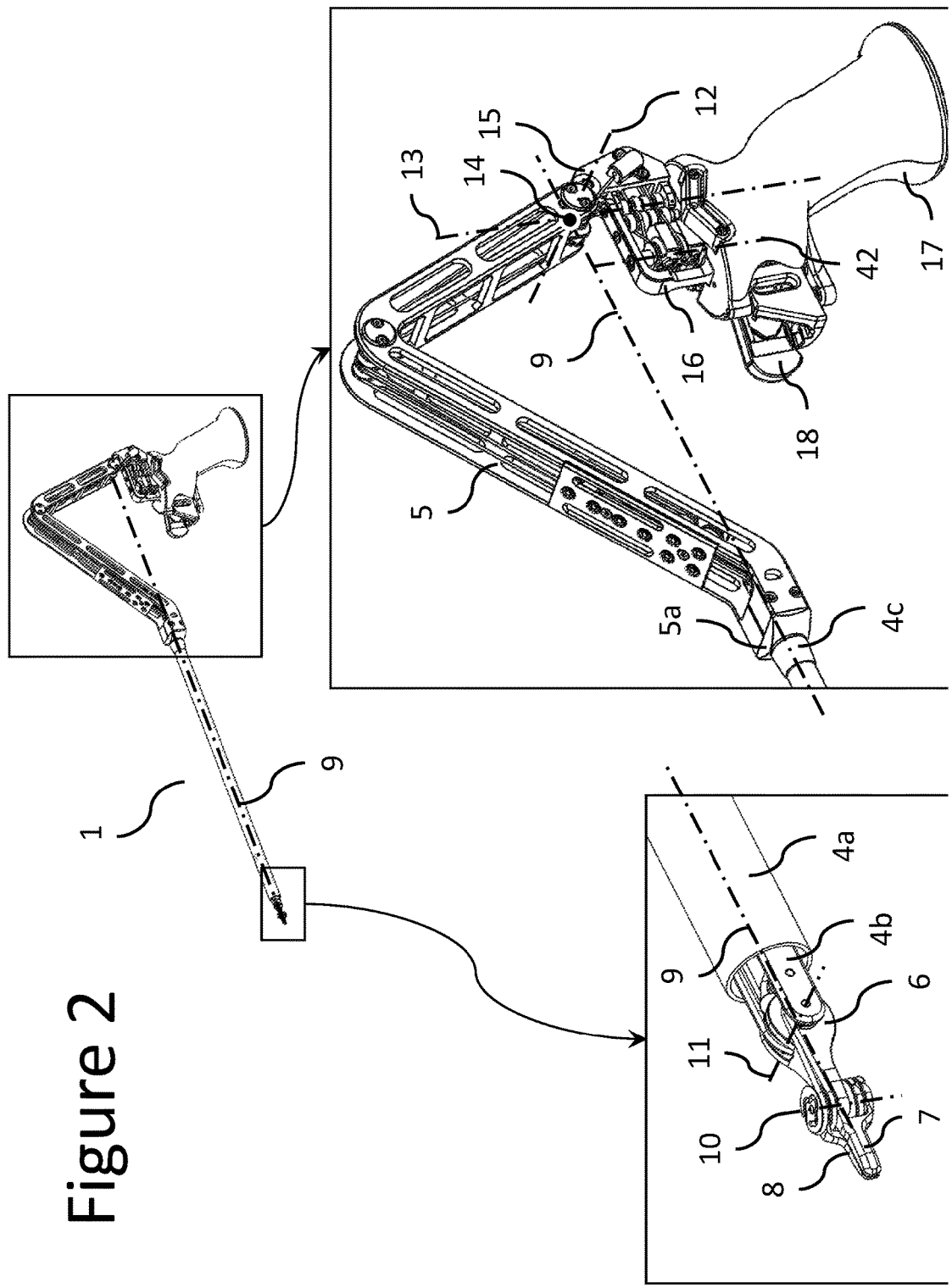
FIG. 2 shows a detailed perspective view of the articulated instrument according to an embodiment of the present invention.

According to FIGS. 1, 2, 3 and 4, the articulated instrument 1 comprises: i) a proximal handle 3 having a number of handle links 15, 17, 18 interconnected by a plurality of handle joints, represented by rotations over the axes 12, 13, 42; a ii) a frame 5, structurally connecting the proximal handle 3 to the distal portion of the articulated instrument 1; iii) a distal end-effector 2 having a number of end-effector links 6, 7, 8 interconnected by a plurality of end-effector joints, corresponding to the handle links, and represented by rotations over the axes 11 and 10; and iv) an instrument shaft 4, connecting the distal end of the frame 5 to the distal end-effector 2. More particularly, the kinematic chain formed by the plurality of articulated end-effector links 6, 7, 8 and corresponding end-effector joints 11, 10 of the end-effector 2, may be substantially identical to the kinematic chain formed by the plurality of articulated handle links 15, 17, 18 and corresponding handle joints 12, 13, 42 of the proximal handle 3. As can be seen in FIG. 2, in some embodiments of the present invention, the axes 9, 12, and 13 are perpendicular to each other and intersection at a central rotation point 14, which is kinematically equivalent to a spherical joint.

Figure 3:
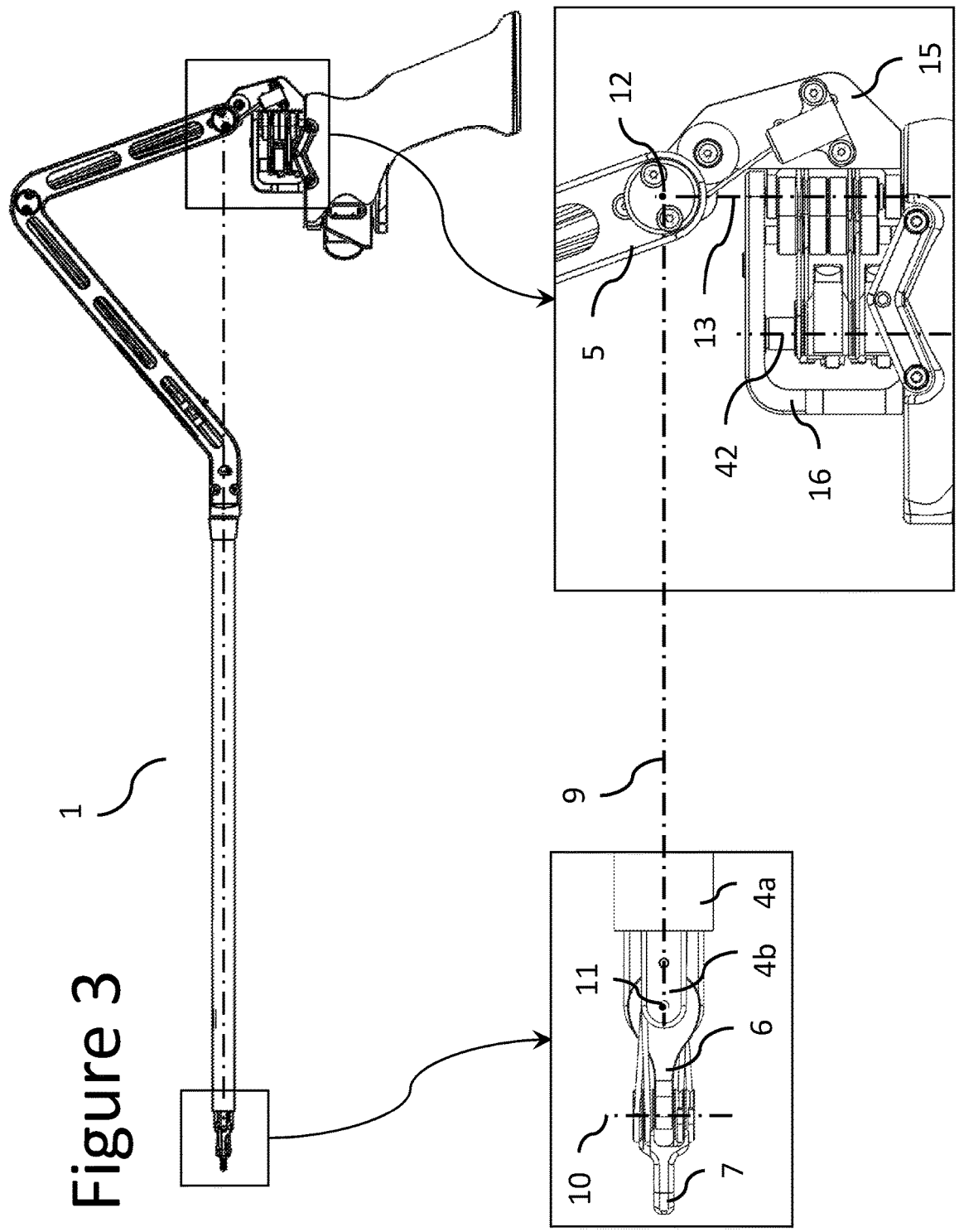
FIG. 3 shows a detailed side view of the articulated instrument according to an embodiment of the present invention.
Figure 4:
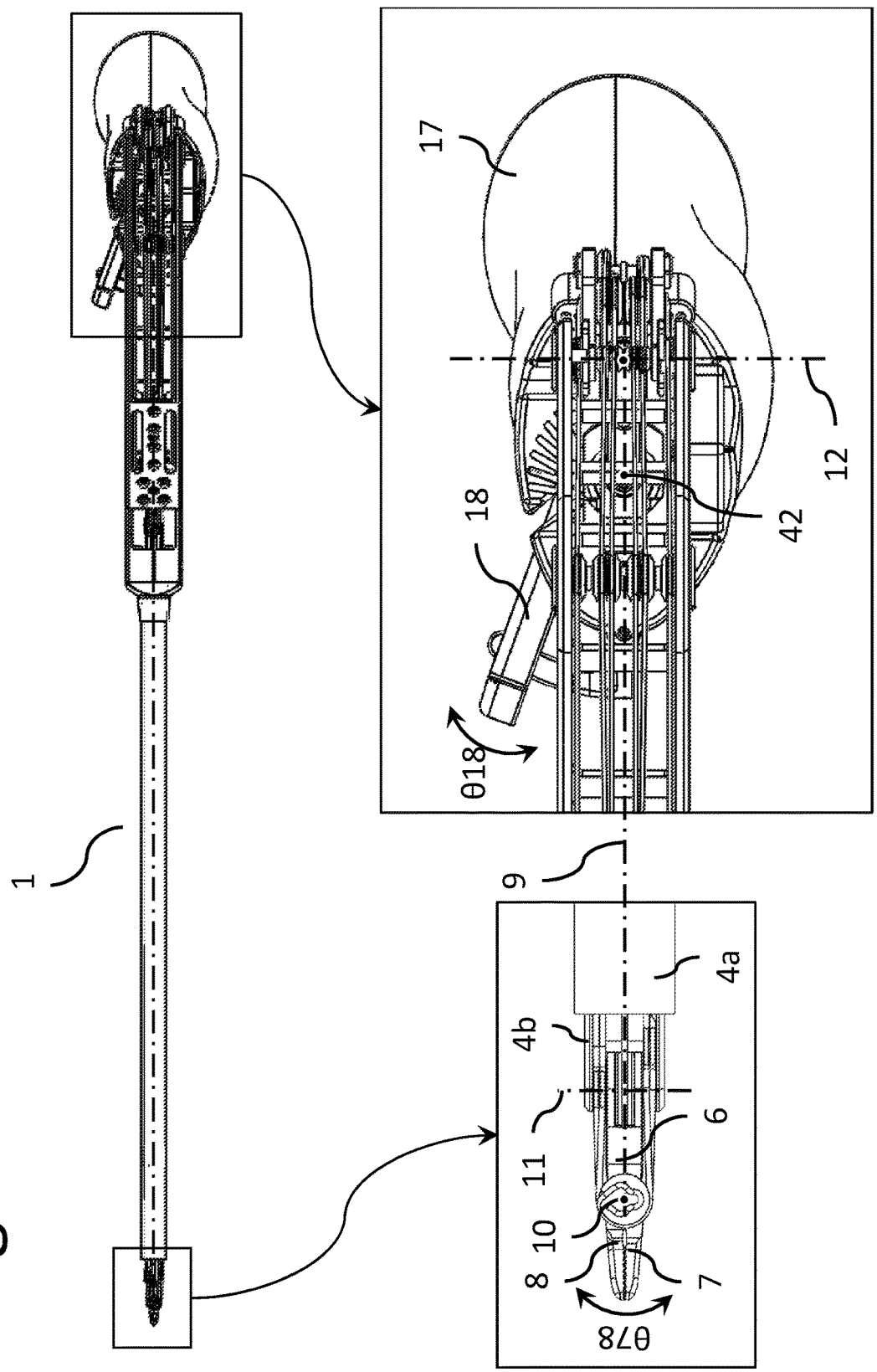
FIG. 4 shows a detailed top view of the articulated instrument according to an embodiment of the present invention.
Figure 7:
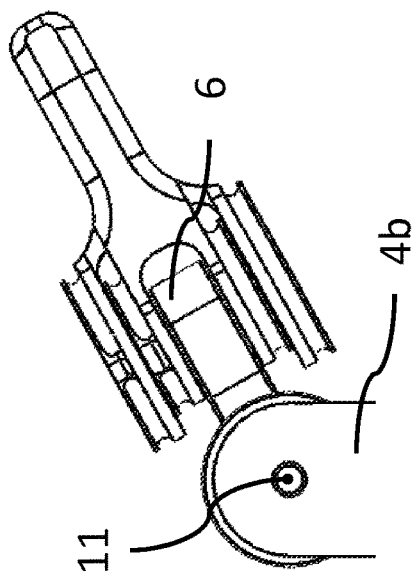
FIG. 7 shows the distal end-effector of the articulated instrument according to an embodiment of the present invention in a third active position.
Figure 6:
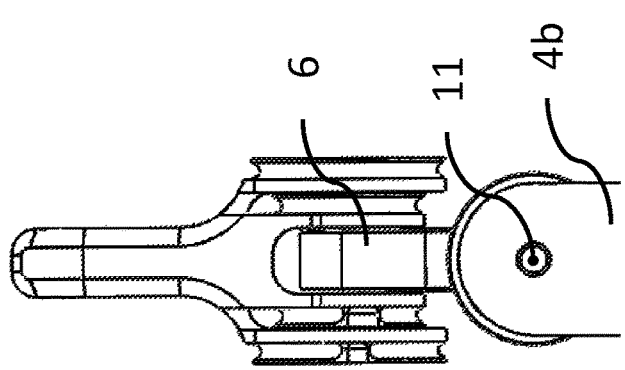
FIG. 6 shows the distal end-effector of the articulated instrument according to an embodiment of the present invention in a second active position.
Figure 5:
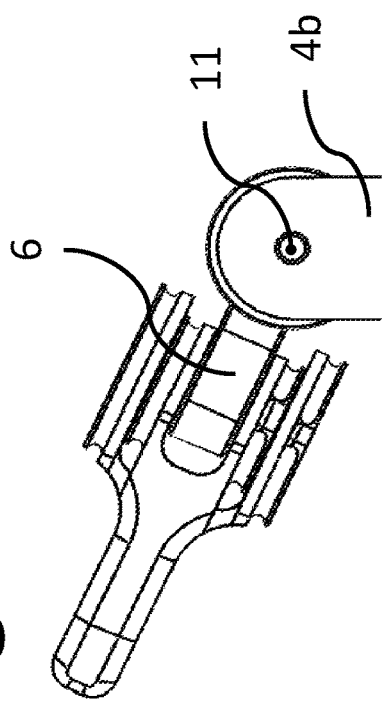
FIG. 5 shows the distal end-effector of the articulated instrument according to an embodiment of the present invention in a first active position.

Referring to FIGS. 2, 3 and 4, the end-effector 2 is connected to the distal extremity of the instrument shaft 4 by a proximal end-effector joint, which allows the rotation of the proximal end-effector link 6 by the proximal axis 11 in such a manner that the orientation of the proximal end-effector link 6 with respect to the main axis 9 of the instrument shaft 4 can be changed. The distal end-effector links 7, 8 are pivotally connected to the proximal end-effector link 6 by two distal joints, having coincident axes of rotation, which are represented by the distal axis 10. This distal axis 10 is substantially perpendicular and non-intersecting with the proximal axis 11 and substantially intersects the main axis 9 of the instrument shaft 9. FIGS. 5 to 7 show the end-effector 2 with different angular displacements at the proximal end-effector link 6.

Figure 9:
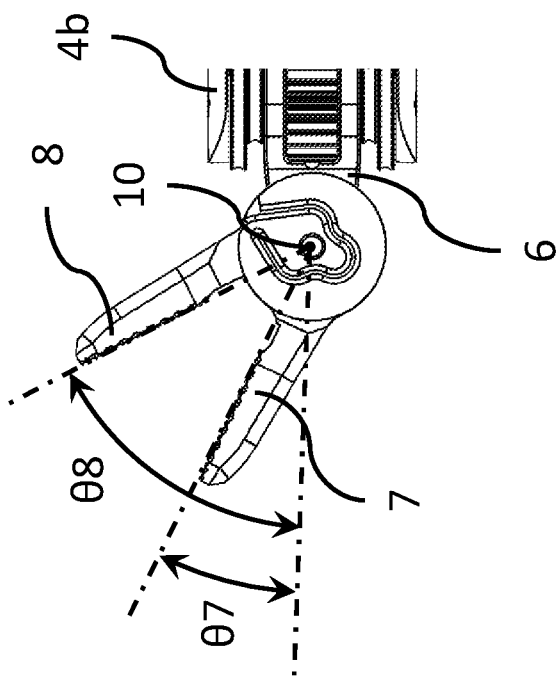
FIG. 9 shows the distal end-effector of the articulated instrument according to an embodiment of the present invention in a fifth active position.
Figure 8:
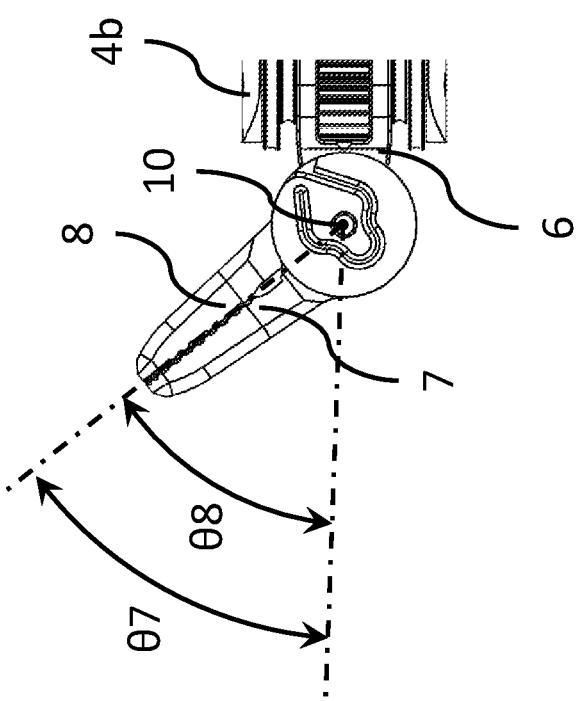
FIG. 8 shows the distal end-effector of the articulated instrument according to an embodiment of the present invention in a fourth active position.

By actuating the two distal joints, the two distal end-effector links 7, 8 can be angulated over the distal axis 10, with respect to the plane containing the main axis 9 and the distal axis 10, by the angles θ7, θ8. Consequently, through the combination of rotations θ7 and θ8, it is possible to operate the surgical instrument 1, in such a manner as to provide orientation motions between the end effector and the instrument shaft 4 (FIG. 8) and to accomplish its "open/close" function (FIG. 9).

The articulated instrument 1 further comprises mechanical transmission systems arranged to kinematically connect the distal end-effector 2 with the proximal handle 3 such that the movement (angle of joint) applied on each handle joint of the proximal handle 3 is reproduced by the corresponding end-effector joint of the distal end-effector 2.

Figure 10:
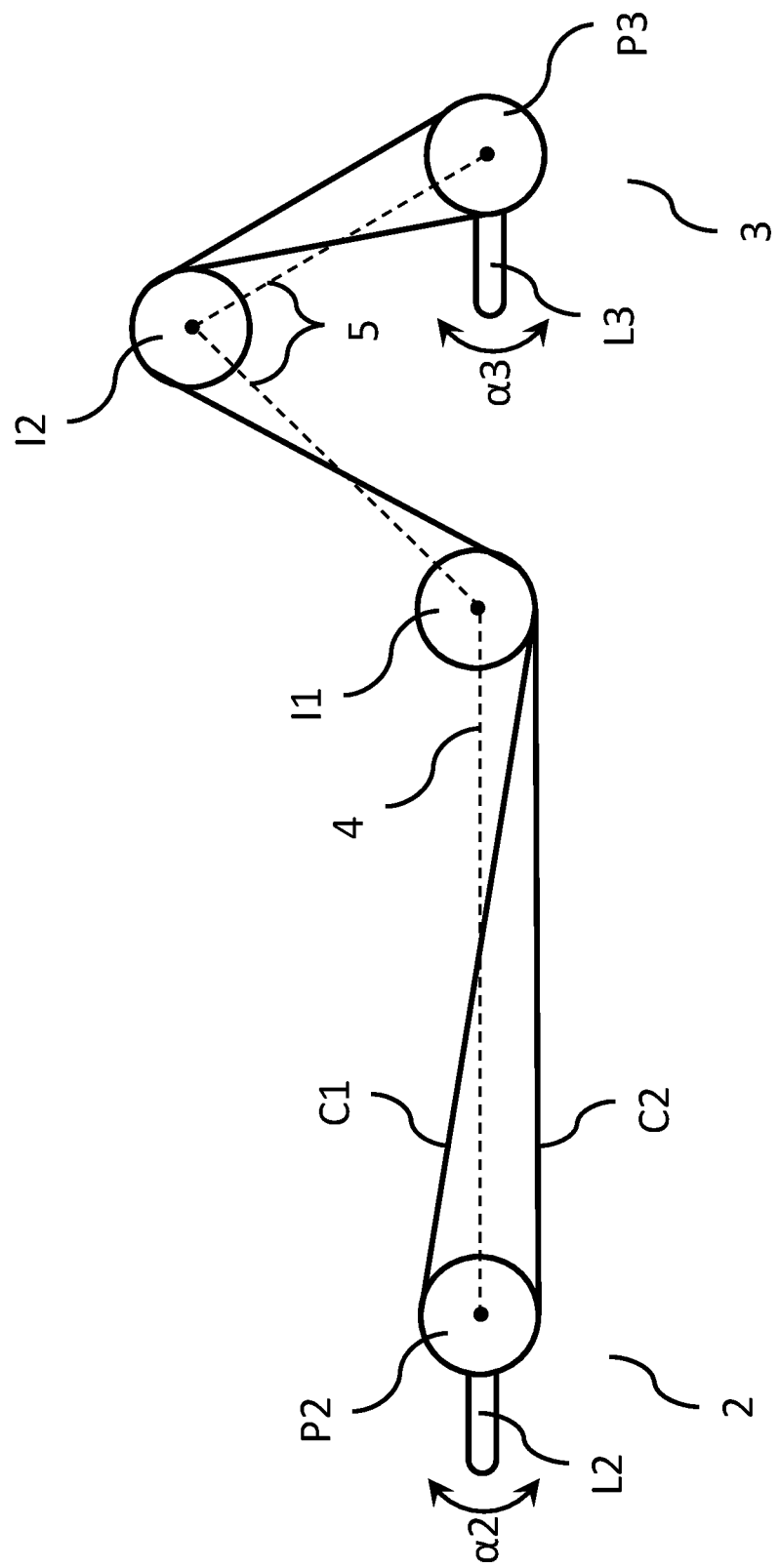
FIG. 10 shows a simplified path of a flexible transmission system actuating a distal end-effector articulation of the articulated instrument according to an embodiment of the present invention.

For each degree of freedom of the articulated instrument 1, different types of mechanical transmission can be used. In order to minimize the system's overall friction and inertia, certain embodiments of the current invention may use a mechanical transmission in the form of pulley-routed flexible elements, where each driven pulley of the distal end-effector 2 is connected to the respective driving pulley of the proximal handle 2, by a closed cable loop transmission. As can be seen in FIG. 10, the action of the user creating a rotation α3 on a general handle link L3 produces a rotation α3 on the handle pulley P3, which is directly connected to the handle link L3. Then, the mechanical transmission system, composed by the closed cable loop comprising cables C1 and C2, passes by the frame 5 and the instrument shaft 4 and is able to kinematically connect the handle pulley P3 to the end-effector pulley P2 (a system of idle pulleys I1, I2 is used to guide the cables C1, C2 on their path). As a result, the user actuation α3 on the handle link L3 is reproduced by the rotation α2 of the handle link L2. Depending of the use of amplification elements, α2 may be smaller, bigger or the same as α3.

The transmission of the movement between each handle pulley and the corresponding end-effector pulley in the aforementioned embodiments, by using this kind of mechanical transmission, may present certain drawbacks pertaining to kinematic and dynamic coupling between the driven and the driving pulleys. Furthermore, the adoption of a closed loop cable transmission requires that the overall length of the cable route must be kept constant, for all possible handle/end-effector configurations, independently of the motion performed by the driving pulleys of the articulated handle 2. In this sense, the aforementioned embodiments of the present invention will be operational but may not accommodate all possible use cases.

Figure 42:
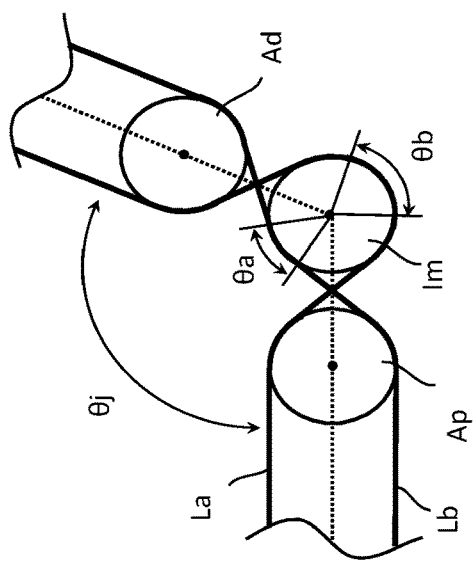
FIG. 42 shows a schematic view of a cable rooting method to maintain a closed loop with a constant length, shown at the joint level, in accordance with various embodiments of the present invention.

Therefore, cables must be routed through joint idler pulleys while maintaining constant cable length. The basics of the cable routing method used in this invention is illustrated in FIG. 42 for the general case of having both cables La and Lb, composing the closed loop L, being routed through a general pivot joint. The cables La and Lb are wrapped around a set of pulleys, Im, called the "joint idler pulleys," which are concentric with the joint's axis of rotation. To maintain constant cable length of the closed loop, cables La, Lb must remain in contact with the joint idler pulleys at all times. In this way, if the joint angle θj is reduced, the length of the superior segment of La, in contact with the idler pulley Im will decrease and the inferior segment of Lb will increase, by the same value, guaranteeing the constant length of the cable closed loop. In addition, in order to keep a permanent contact between the cables La and Lb with the idler pulleys Im, auxiliary pulleys Ap and Ad may be added.

Figure 43:
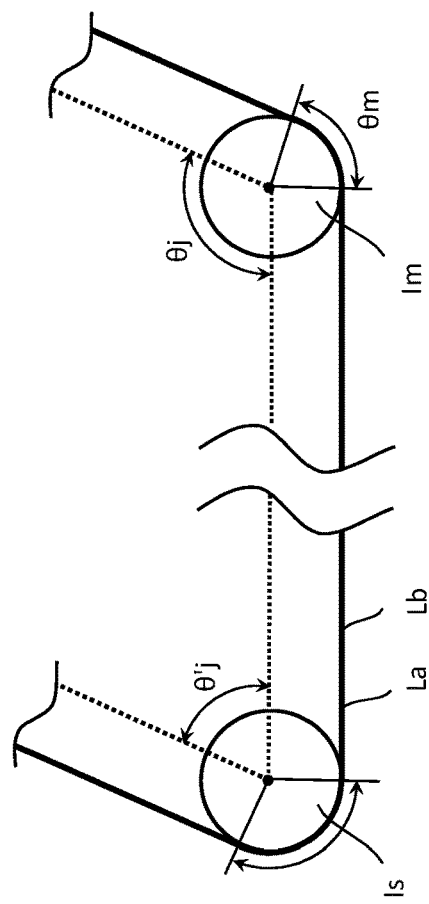
FIG. 43 shows a schematic view of another cable rooting method to maintain a closed loop with a constant length, shown at the level of equivalent handle/end-effector joints, in accordance with various embodiments of the present invention.

Another solution to keep a constant cable length of the closed loop consists in compensating the length change not at the joint level but between the equivalent idler pulleys Im and Is of respective handle and end-effector as schematically shown in FIG. 43. In this case, both cables La, Lb are passing under Im and Is and, when the joint angle $\theta j$, $\theta'j$, is changed, the constant length of the closed loop is guaranteed because the increase/reduction of $\theta s$ is compensated by the reduction/increase of $\theta m$.

Figure 11:
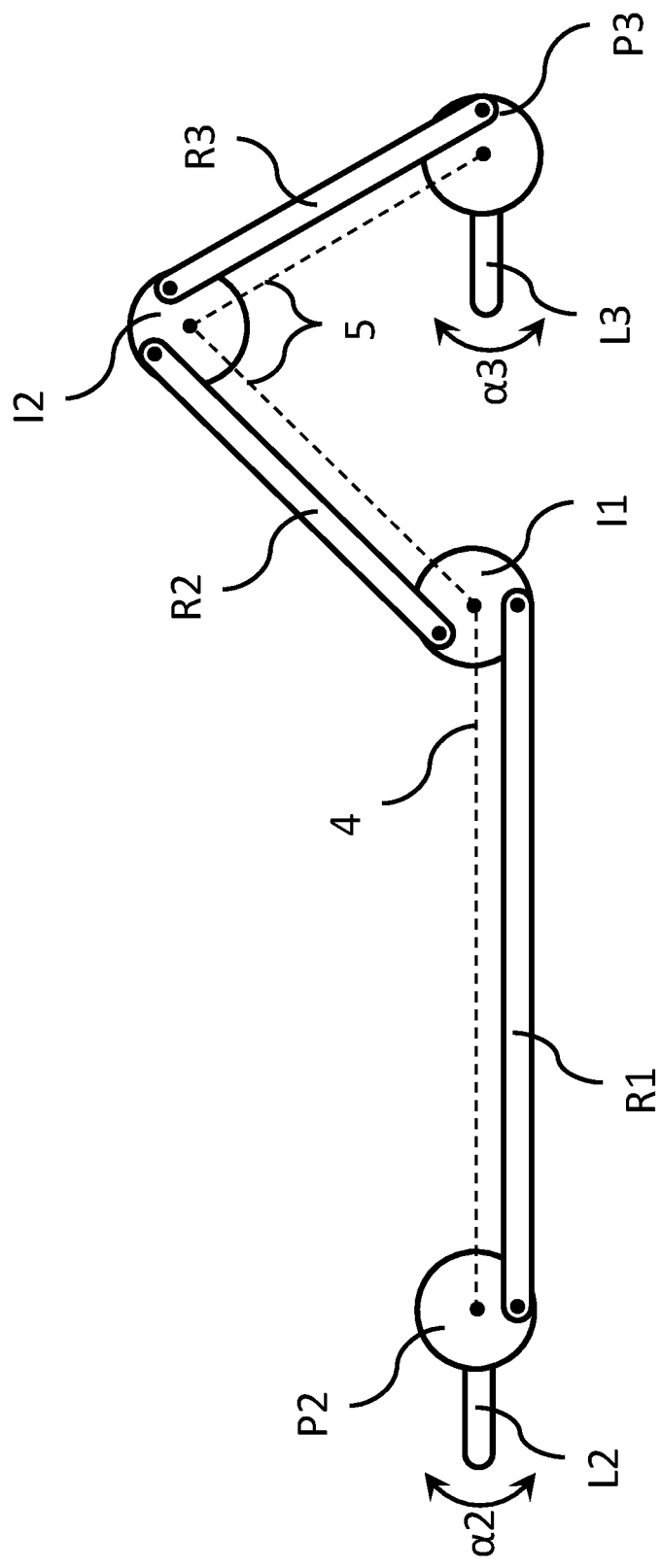
FIG. 11 shows a simplified path of a rigid transmission system actuating a distal end-effector articulation of the articulated instrument according to a different embodiment of the present invention.

In a different embodiment, as is conceptually illustrated in FIG. 11, the mechanical transmission may comprise rigid elements R1, R2, R3, instead of flexible elements C1, C2, to transmit motion between the handle link L3 and the end-effector link L2. Other embodiments can be achieved by combining flexible elements with rigid elements and/or geared components.

FIGS. 12 to 14 show the articulated instrument 1 with different angular displacements at the proximal handle link 15 (and therefore, proximal end-effector link 6). The geometry of frame 5 allows for the movement of the handle 3 in its full range of motion.

Figure 15:
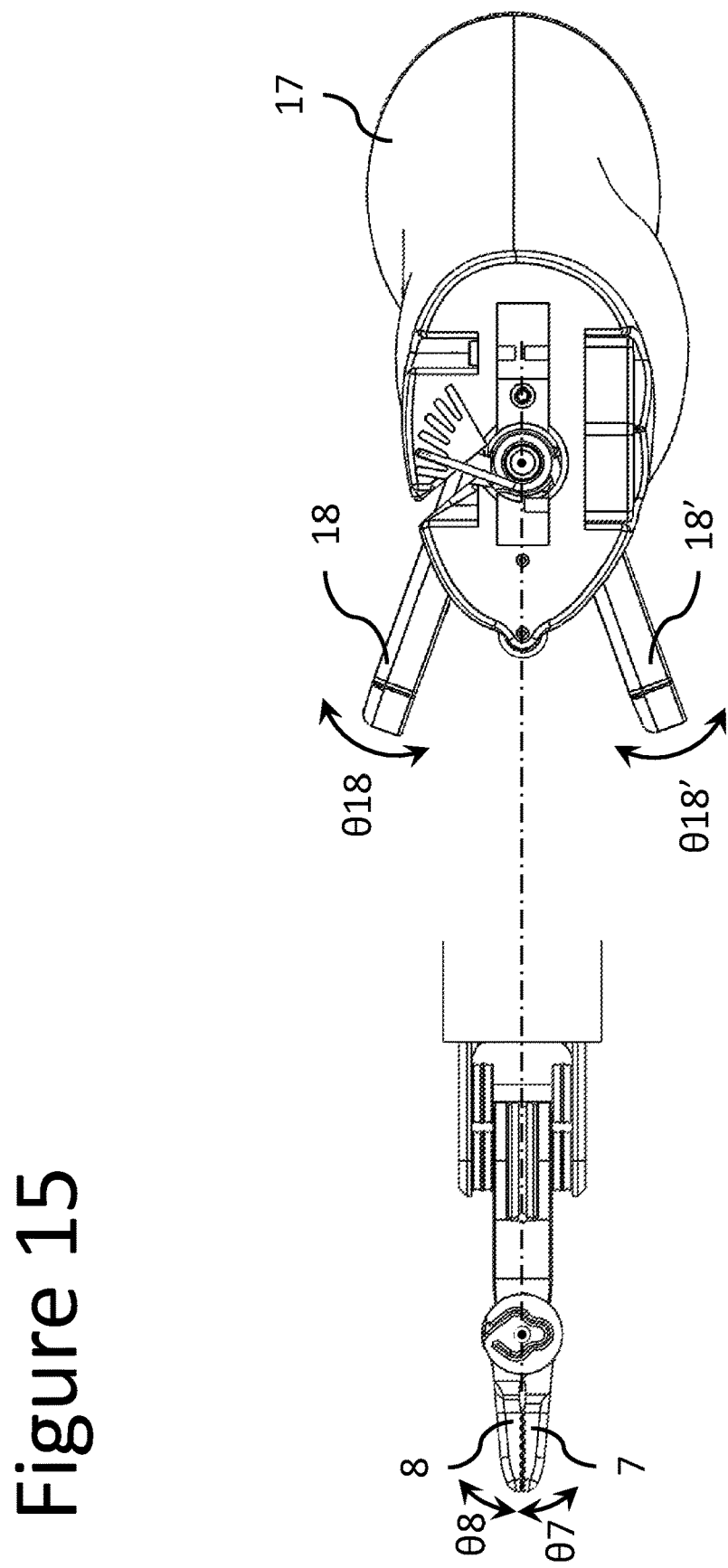
FIG. 15 illustrates the actuation of the two distal end-effector links of the articulated instrument according to an embodiment of the present invention.

In the preferred embodiment of the current invention, the actuation $\theta 18$ of the handle link 18 is able to produce simultaneous rotations $\theta 7$, $\theta 8$ on both the end-effector links 7, 8, with a certain movement amplification ratio. However, as shown in FIG. 15, a second distal handle link 18' may exist, so that its actuation $\theta 18'$ can actuate the end-effector link 7 by a rotation $\theta 7$ and the actuation $\theta 18$ of the handle link 18 is actuating uniquely the end-effector link 8 by a rotation $\theta 8$.

Figure 27:
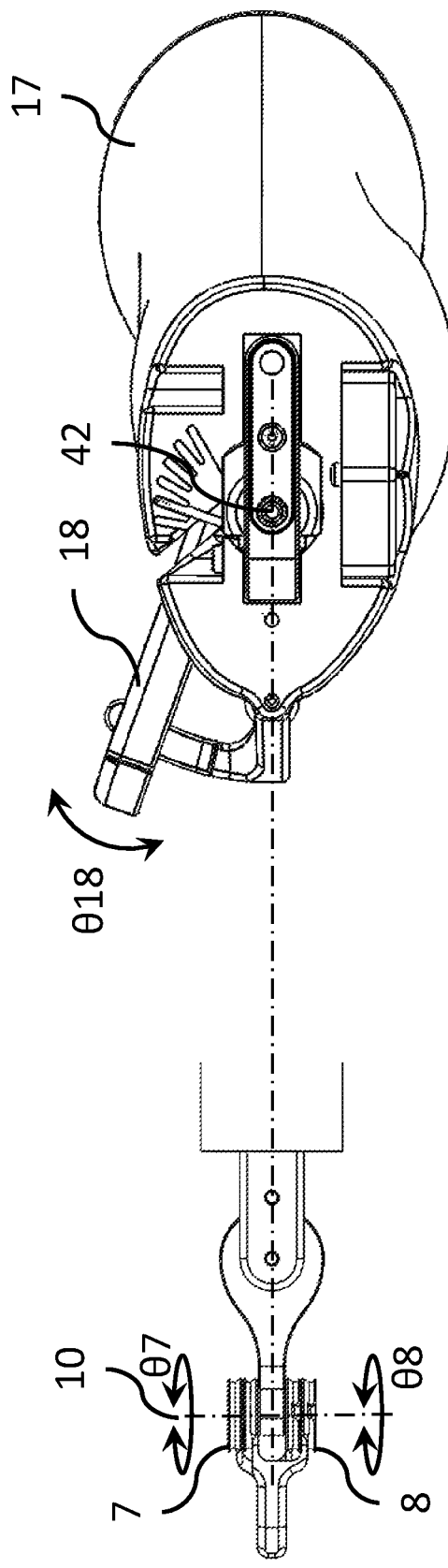
FIG. 27 illustrates the actuation of the two distal end-effector links of the articulated instrument according to an embodiment of the present invention.
Figure 28:
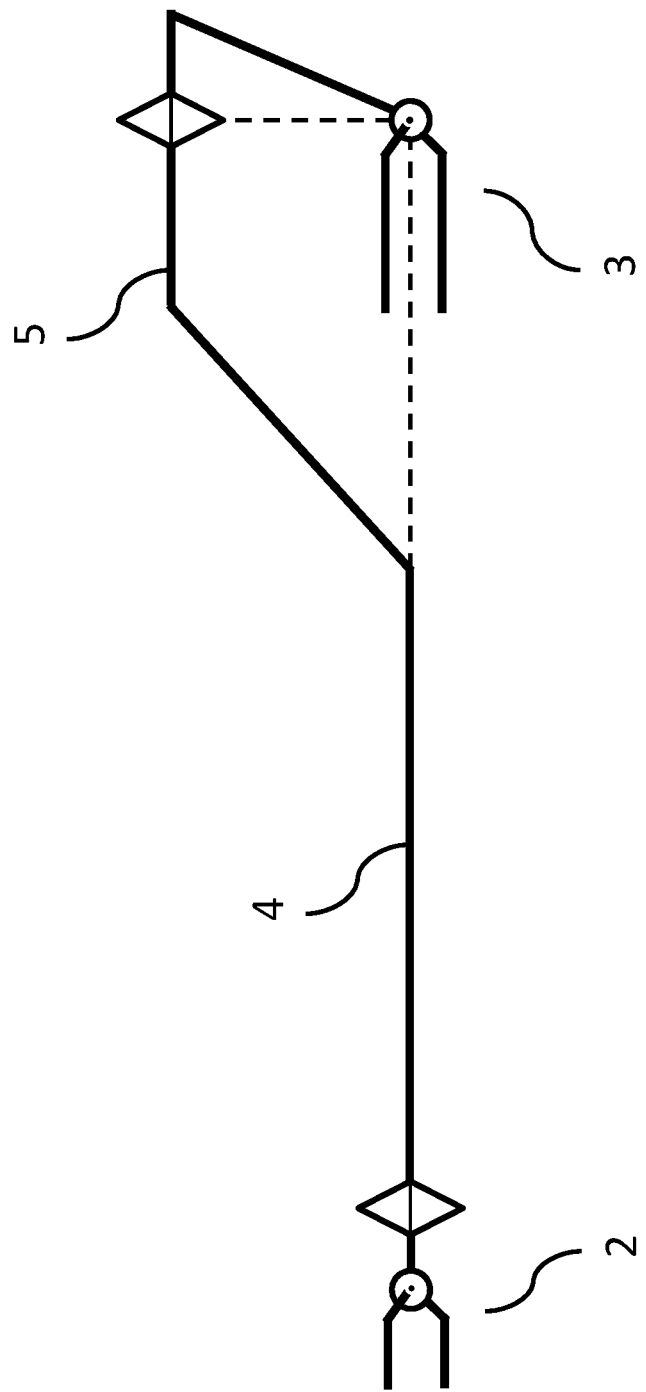
FIG. 28 shows an alternative kinematics of the articulated instrument according to an embodiment of the present invention.
Figure 29:
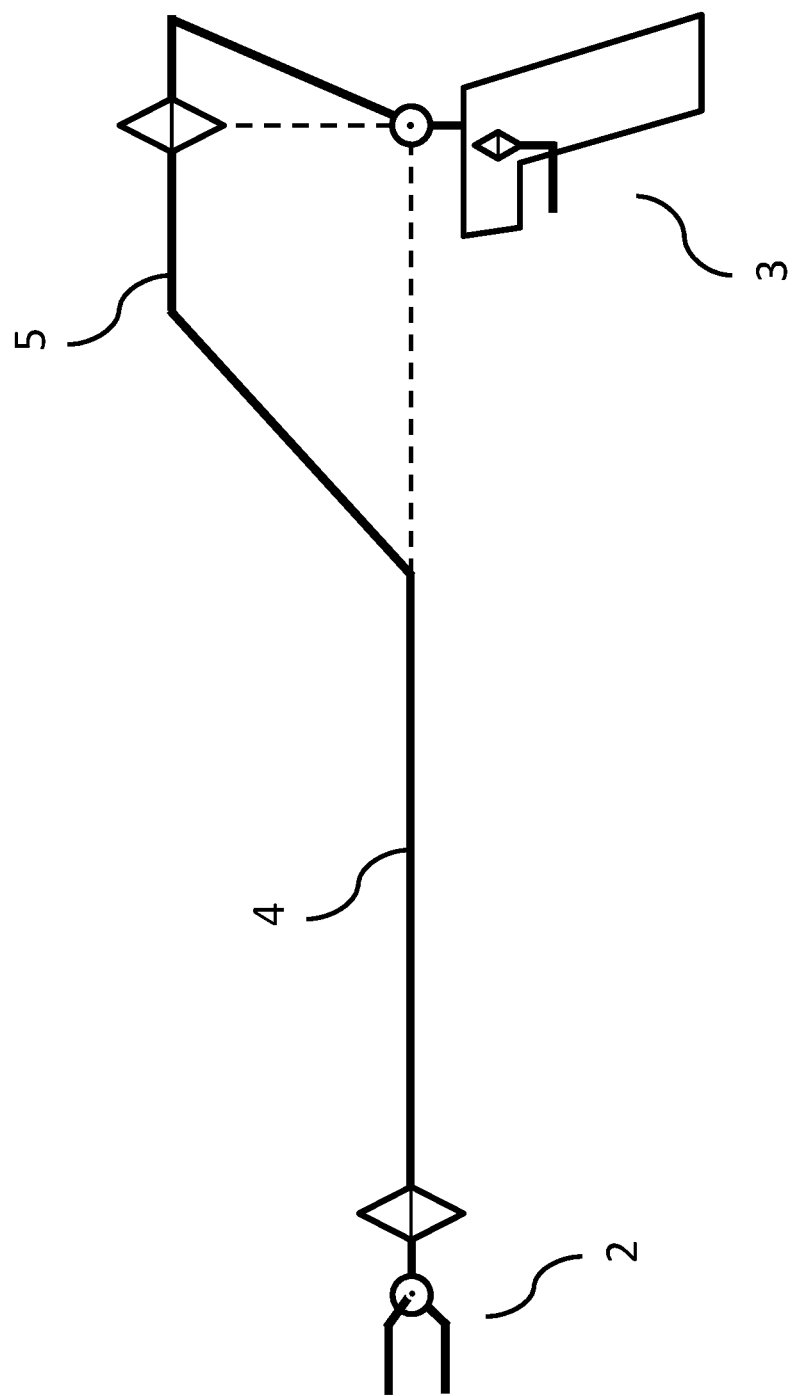
FIG. 29 shows an alternative kinematics of the articulated instrument according to an embodiment of the present invention.
Figure 30:
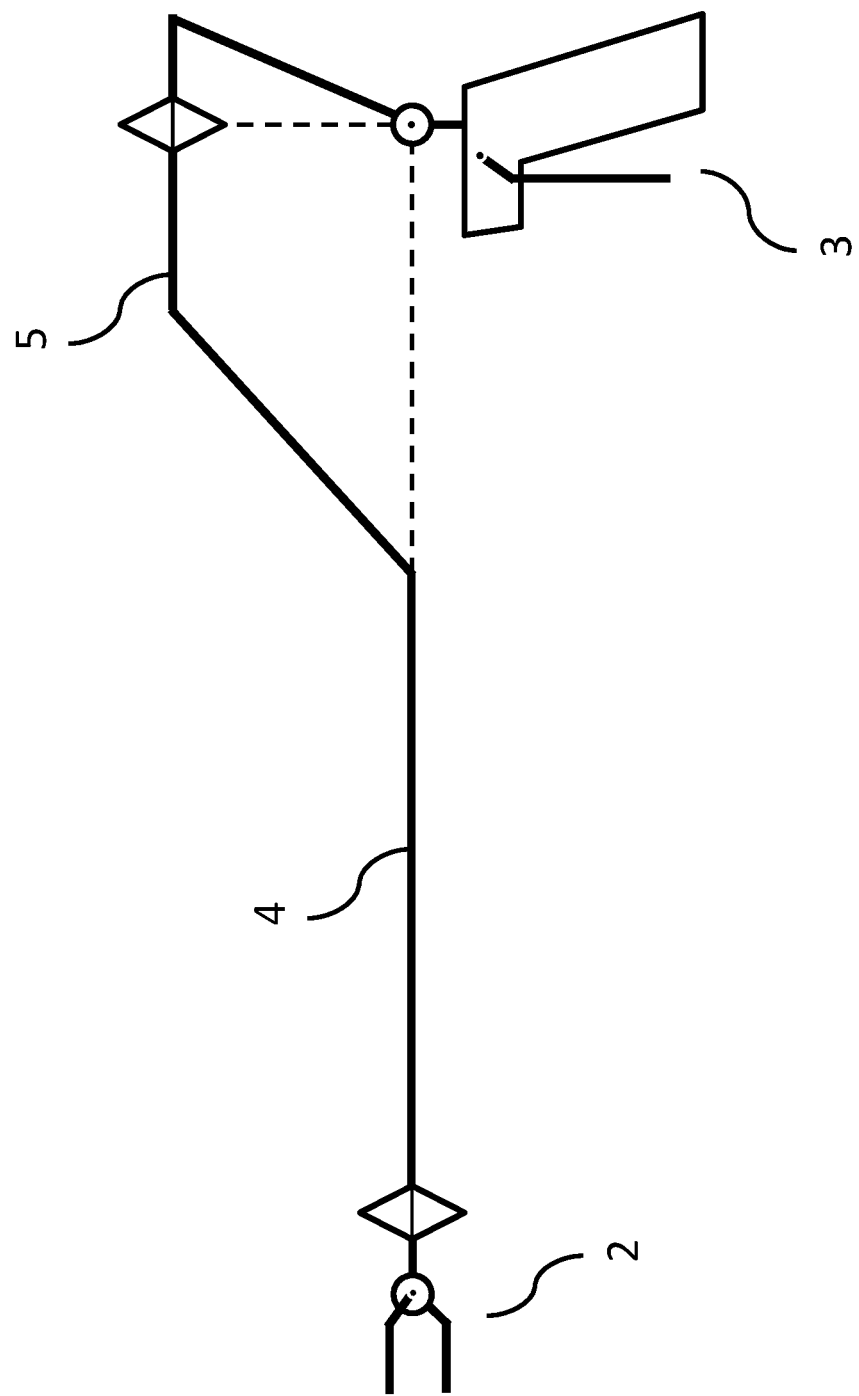
FIG. 30 shows an alternative kinematics of the articulated instrument according to an embodiment of the present invention.
Figure 31:
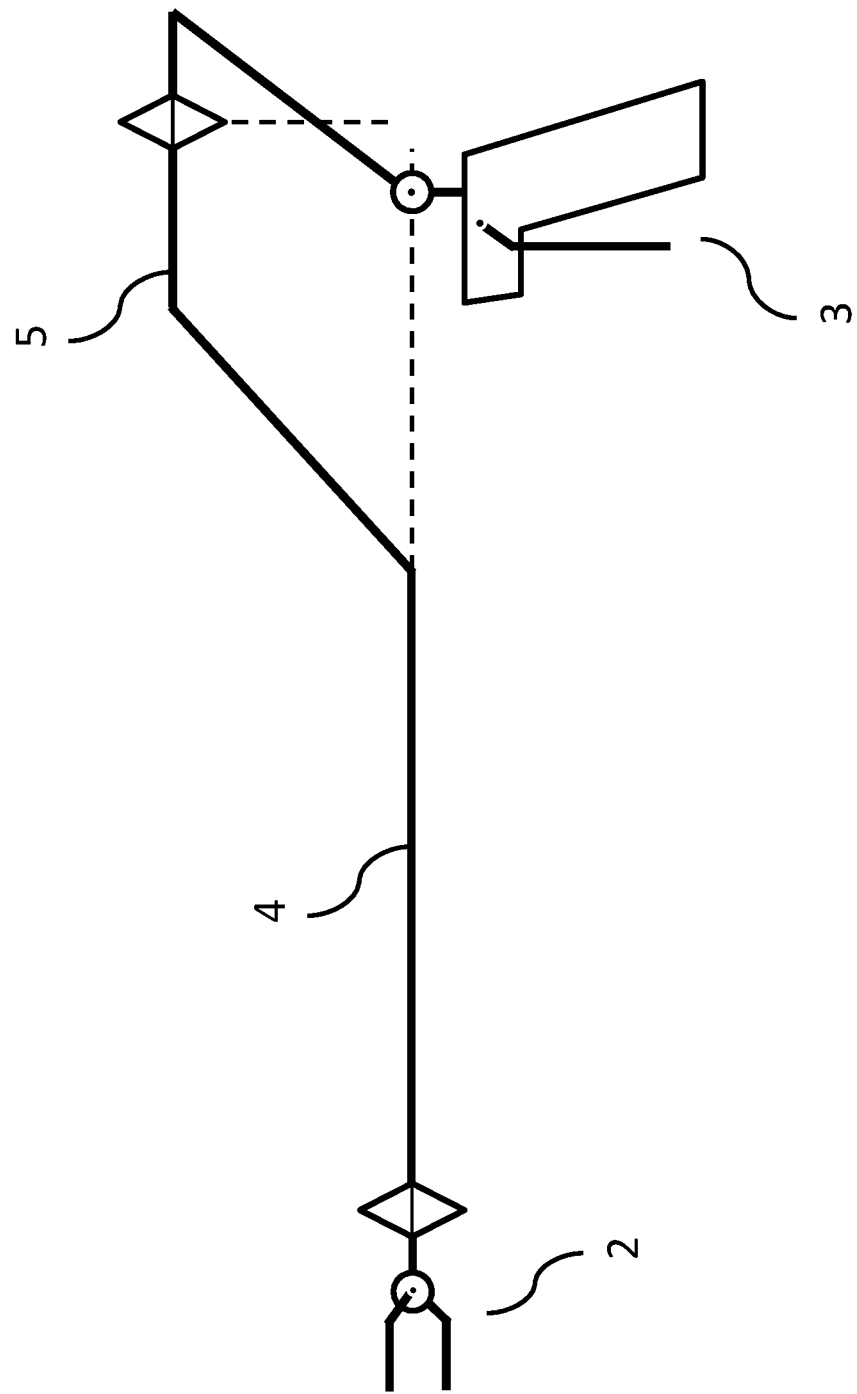
FIG. 31 shows an alternative kinematics of the articulated instrument according to an embodiment of the present invention.

In a different embodiment of the current invention, as shown in FIG. 27, the axis 42, around which the handle link 18 is able to rotate $\theta 18$ might be not parallel to the axis 10 around which the distal end-effector links 7, 8 are moving $\theta 7$, $\theta 8$, providing a different ergonomic position to the user. FIGS. 28 to 31 show alternative kinematics of the articulated instrument 1 according to different embodiments of the present invention.

Figure 16:
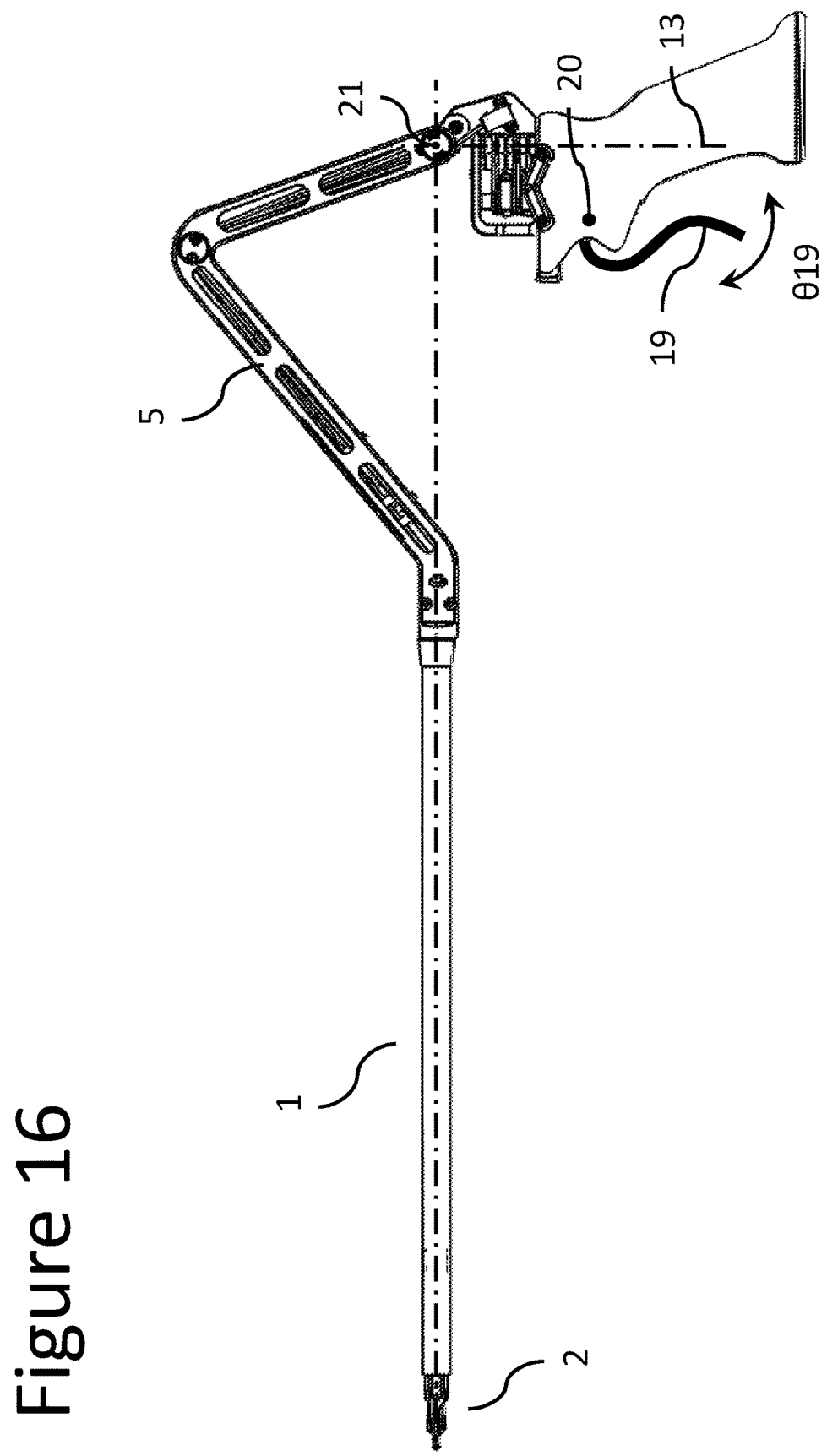
FIG. 16 shows a schematic side view of the articulated instrument, according to an embodiment of the current invention.

In another embodiment of the current invention, the handle link 18 may be replaced by another handle link 19, whose axis of rotation 20 is perpendicular and non-intersecting with the axis 13 (FIG. 16), providing a different ergonomy to the user.

Figure 17:
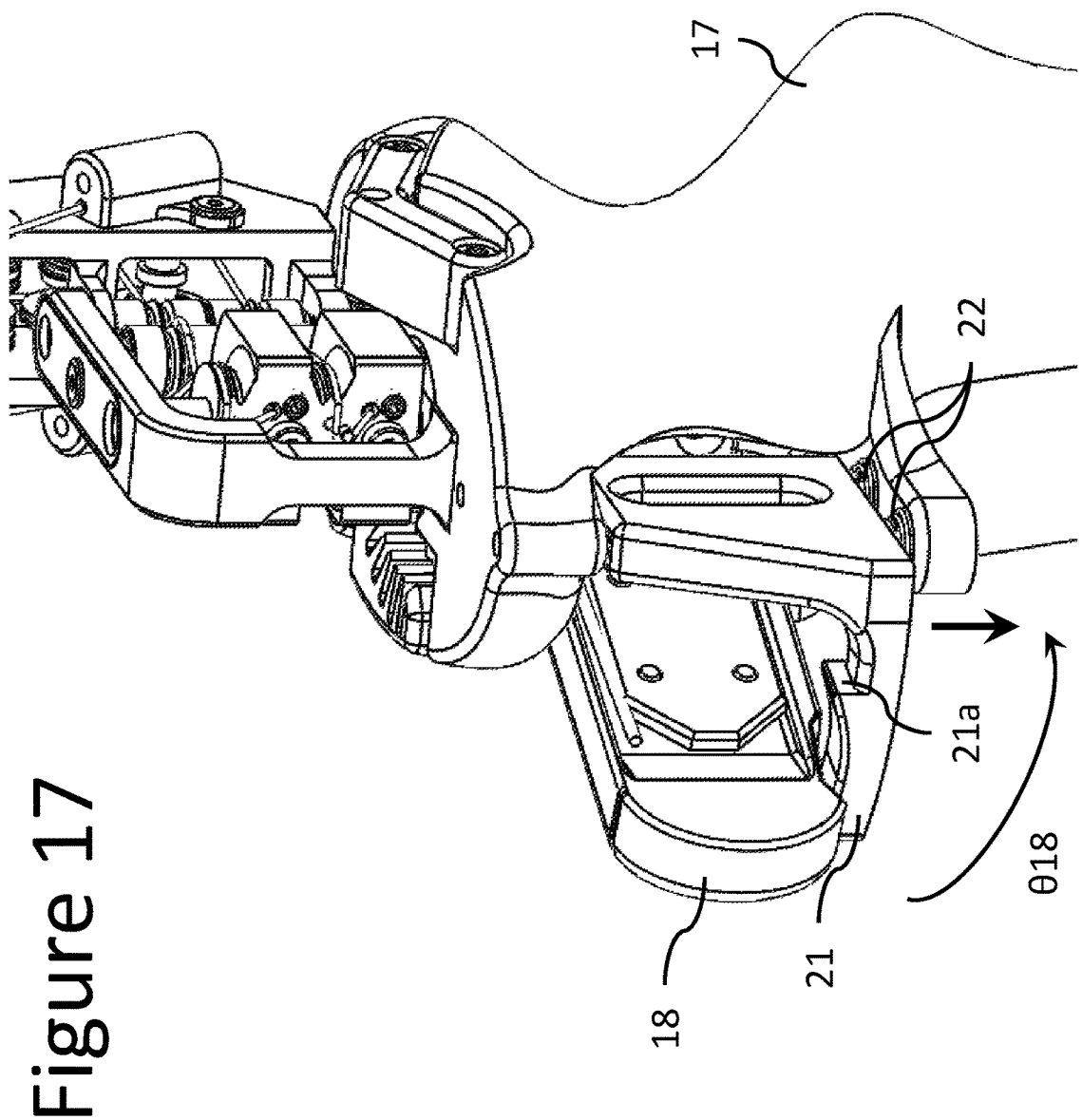
FIG. 17 shows a perspective view of a clamp system used in the proximal handle of the articulated instrument, according to an embodiment of the current invention.

As can be seen in FIG. 17, a clamp element 21 may be used on the handle 3 in order to block the movement of the handle link 18 when it is brought to the "closed" position. This is particularly useful when the end-effector comprises a needle holder instrument and the user wants to apply high and constant gripping forces on needles when performing suturing tasks. Therefore, when the handle link 18 is brought $\theta 18$ to its "closed" position, its movement is blocked by a wedge/step geometry 21a (actuated by a system of miniature springs 22) of the clamp element 21 (FIG. 17). Then, in order to unlock the movement of the handle link 18, the user should press the clamp element 21 downwards, so that the handle link 18 can pass back through the wedge/step geometry 21a of the clamp element 21.

Figure 18:
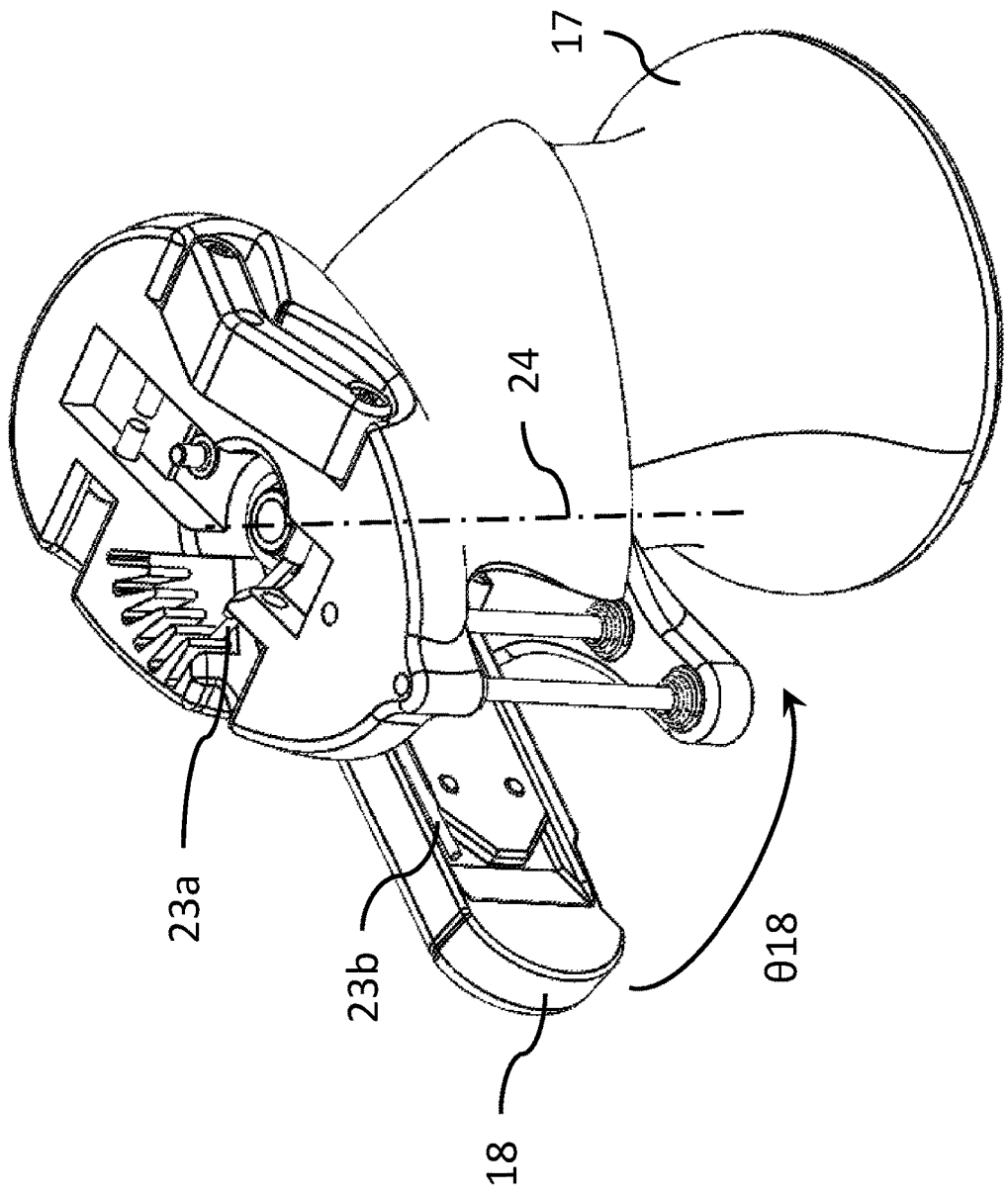
FIG. 18 shows a perspective view of a spring system used in the proximal handle of the articulated instrument, according to an embodiment of the current invention.

In another embodiment, the handle 3 may be provided with a spring element 23 that can bring the handle link 18 to an "opened" default position (FIG. 18) and apply a resistance torque when the handle link 18 is moving towards a "closing" direction.

Figure 19:
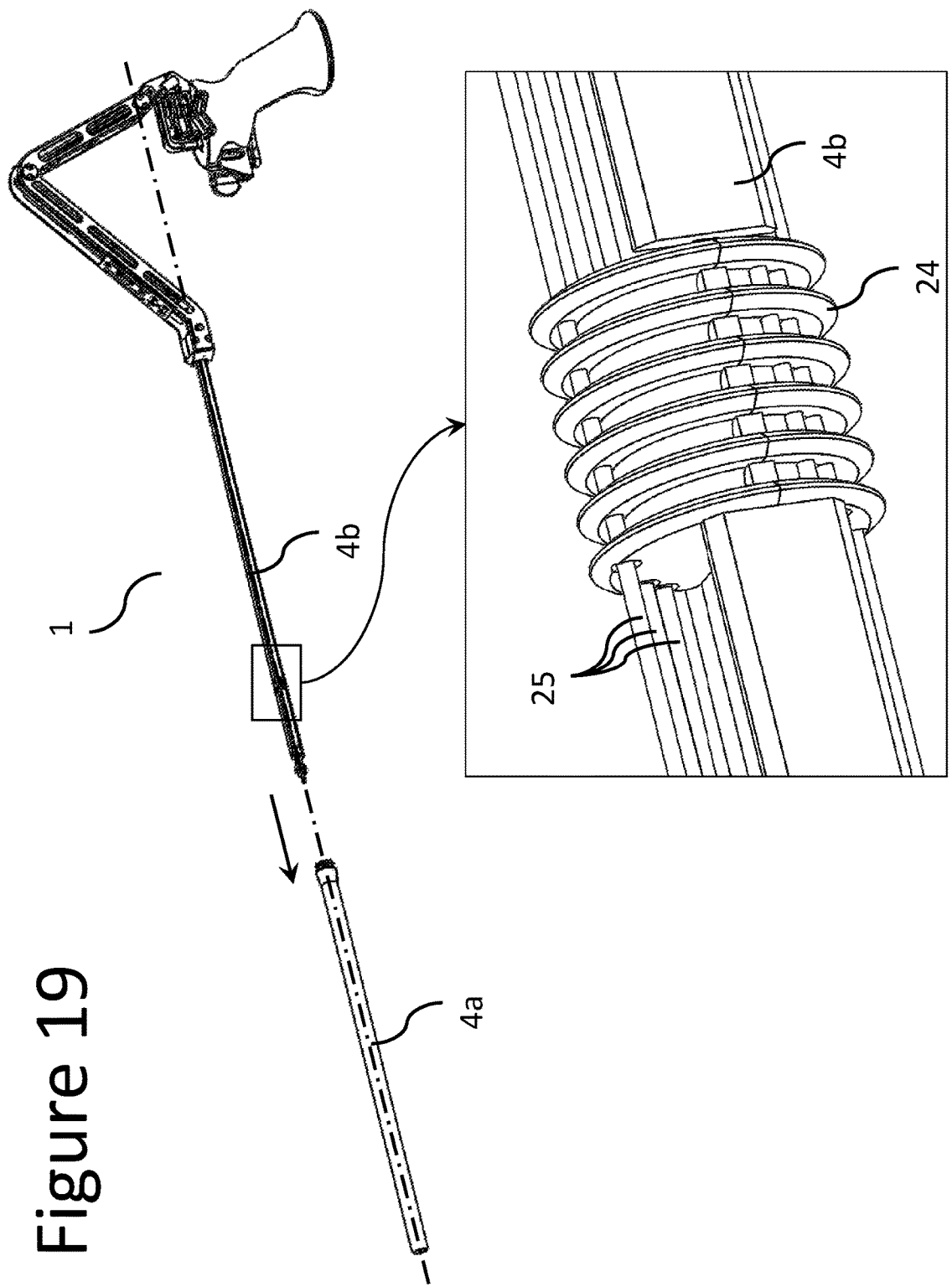
FIG. 19 shows a procedure through which an external tube of an instrument shaft can be assembled and disassembled on the articulated instrument according to an embodiment of the present invention.

As can be seen in FIG. 19, the external tube 4a, composing the instrument shaft 4, can be easily and individually detached and attached to the articulated instrument 1 after each procedure. Referring to FIG. 19, the internal structural element 4b is fixed directly to the frame 5 and the external tube 4a can be connected and disconnected from the internal structural element 4b by threaded surfaces or any other attachment mechanism. Therefore, with this architecture, the external tube 4a can be removed from the articulated instrument 1, without the need to disassemble other parts of the system, like the articulated end-effector 2 or the mechanical transmission elements 25, which remain completely operational without the external tube 4a. This feature facilitates tremendously the procedure to effectively clean and sterilize the articulated instrument 1, which can easily be performed by the hospital staff.

Towards a more distal region of the instrument shaft 4, the external tube 4a is in contact with a sealing element 24, which fills the gap between the internal surface of the external tube 4a and the internal structural element 4b. This sealing element 24 has little channels through which the transmission elements 25 can pass, guaranteeing the airtightness of the articulated instrument 1.

Figure 20:
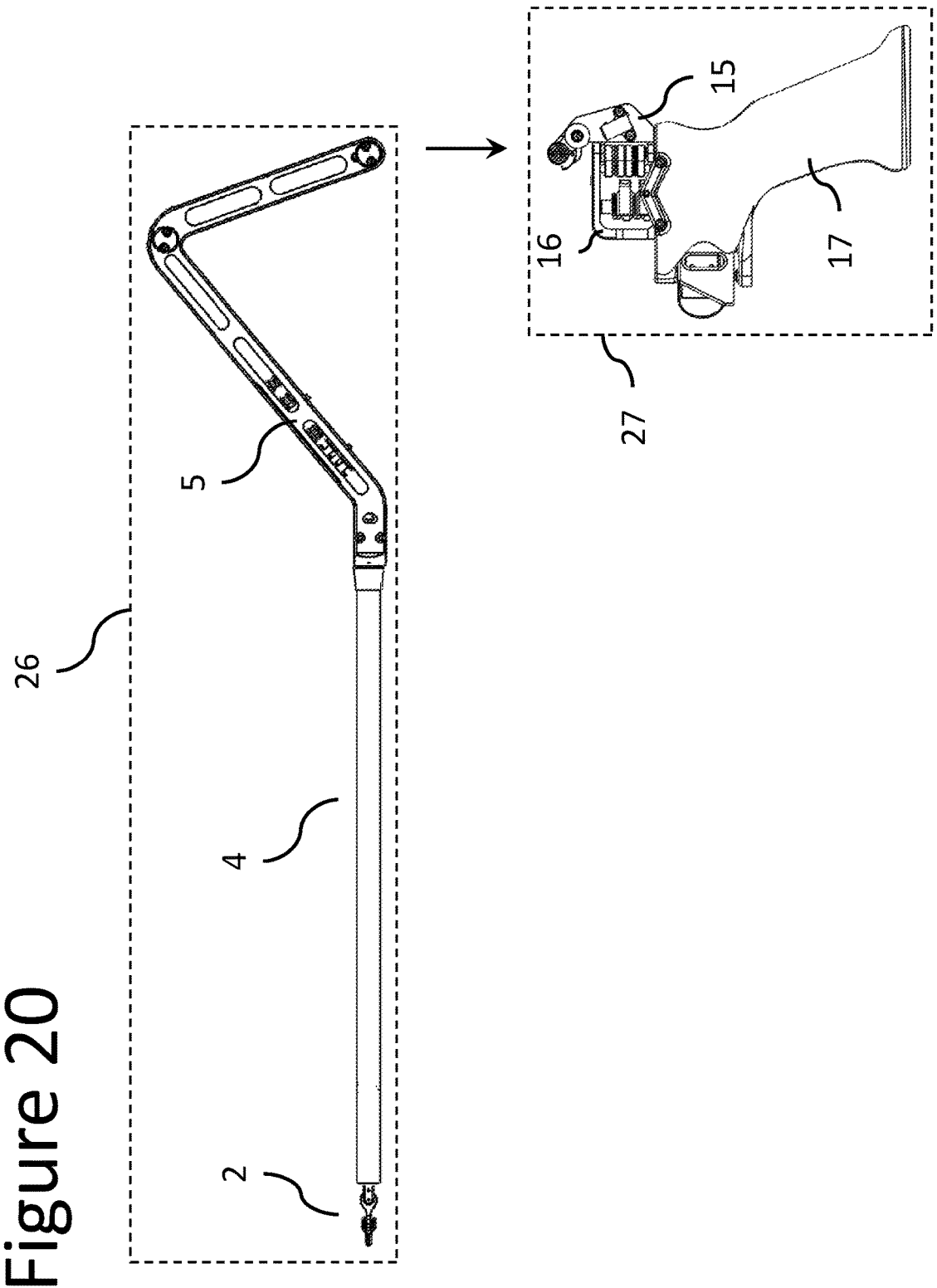
FIG. 20 shows a distal part of an articulated instrument detached from the proximal part of the articulated instrument according to an embodiment of the present invention.
Figure 21:
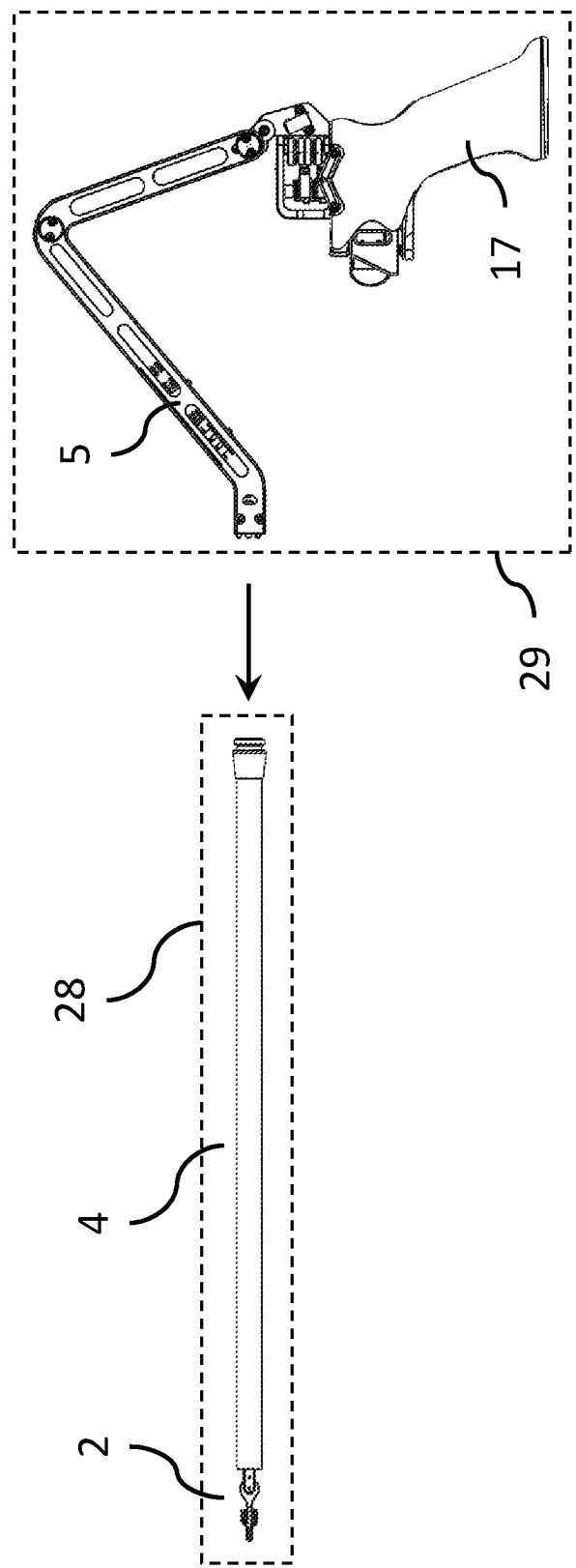
FIG. 21 shows a distal part of an articulated instrument detached from the proximal part of the articulated instrument according to another embodiment of the present invention.

In order to farther facilitate the cleaning and sterilization procedure, the distal part of the articulated instrument 1 may be able to be easily attached and detached to the proximal part of the articulated instrument 1. In one possible embodiment of the current invention, the attachment/detachment between the distal 26 and the proximal 27 parts of the articulated instrument 1 can be done between the frame 5 and the handle 3 (FIG. 20). However, in another embodiment of the current invention, the attachment/detachment between the distal 28 and the proximal 29 parts of the articulated instrument 1 can be done between the instrument shaft 4 and the frame 5 (FIG. 21).

Figure 22:
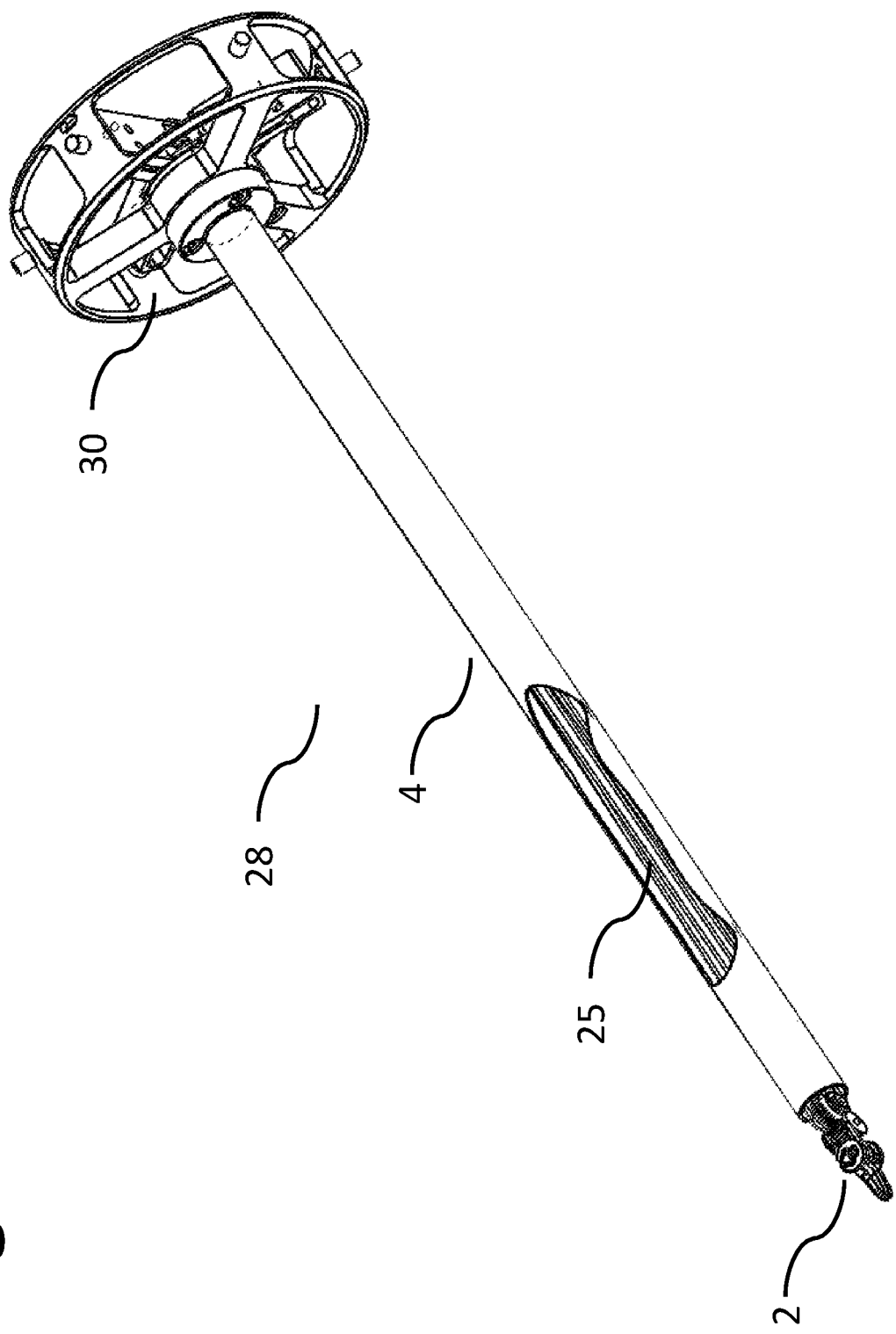
FIG. 22 shows a detachable distal part of an articulated instrument according to an embodiment of the present invention.

In the above mentioned embodiment, the detachable distal instrument 28 may be provided with a distal articulated end-effector 2, a proximal hub 30 and the instrument shaft 4, through which different mechanical elements 25 may pass, delivering motion to the different end-effector links 6, 7, 8 (FIG. 22) from the proximal hub 30.

Figure 23:
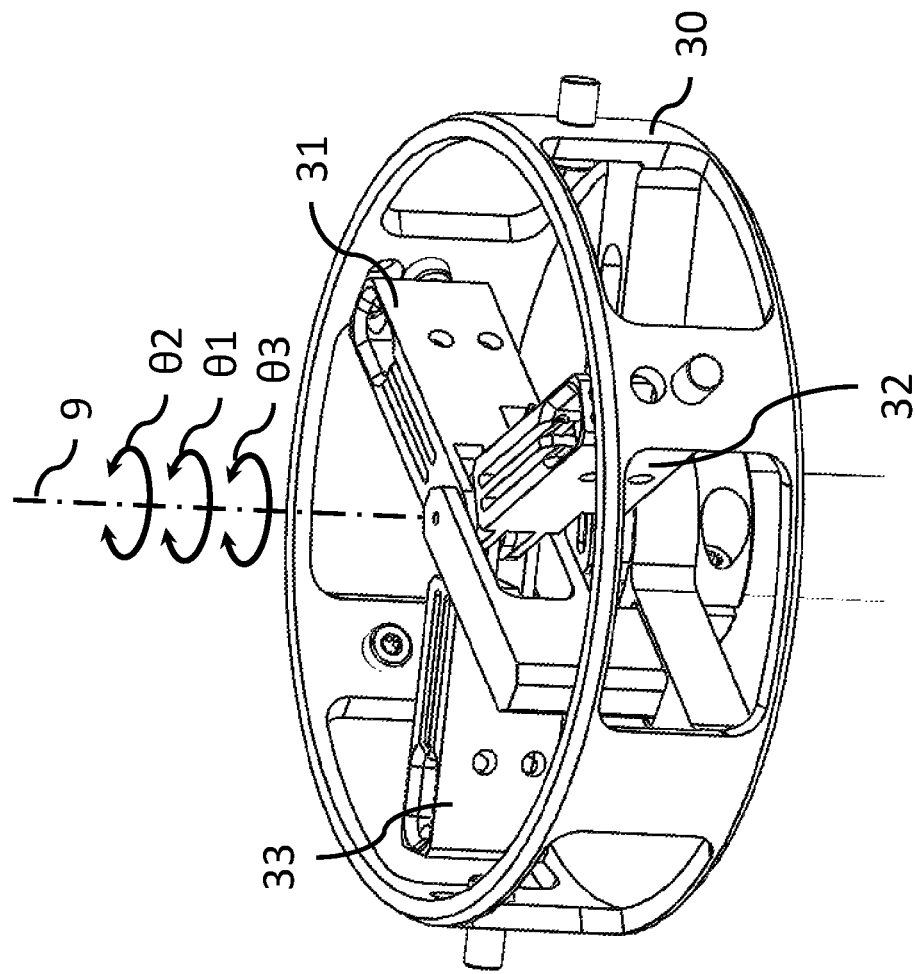
FIG. 23 shows the rotational elements of an interface portion of a distal part of the articulated instrument according to an embodiment of the present invention.
Figure 24:
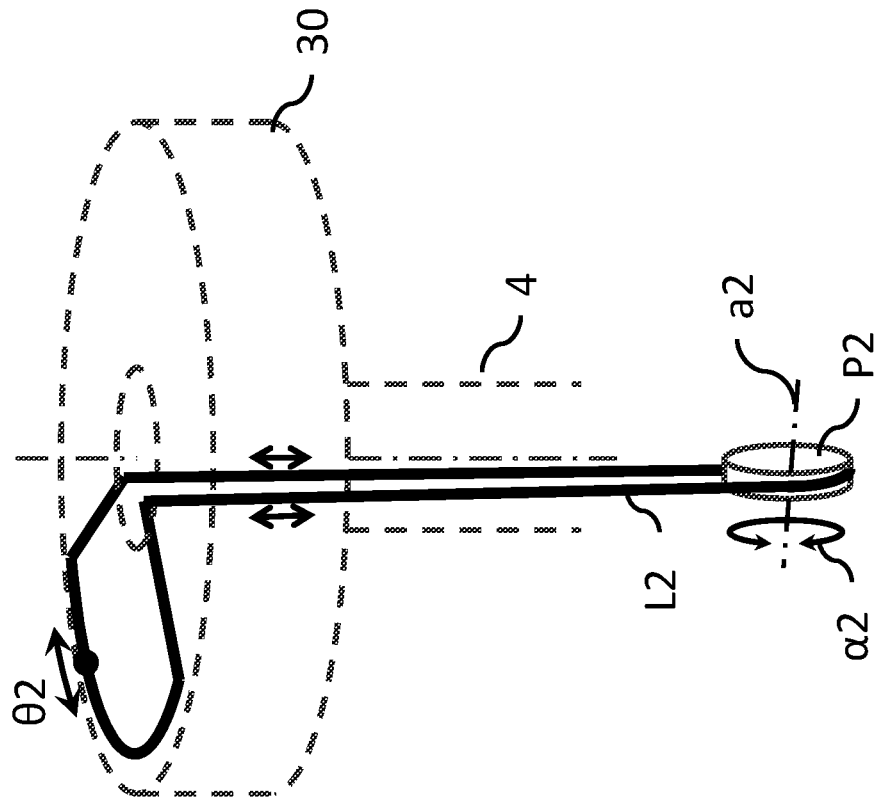
FIG. 24 shows the rotational kinematics of an interface portion of a distal part of the articulated instrument according to an embodiment of the present invention.

With reference to FIGS. 23 and 24, the movement is transmitted to each one of the three distal articulations of the articulated instrument 1 by a rotating element 31, 32, 33, which is able to rotate about the axis 9 and is connected to one of the transmission elements 25. As a result, when the rotating element 31, 32, 33 rotates a certain angle $\theta 1$, $\theta 2$, $\theta 3$ about the axis 9, a rotation $\alpha 1$, $\alpha 2$, $\alpha 3$ is transmitted to the respective end-effector link 6, 7, 8.

Figure 25:
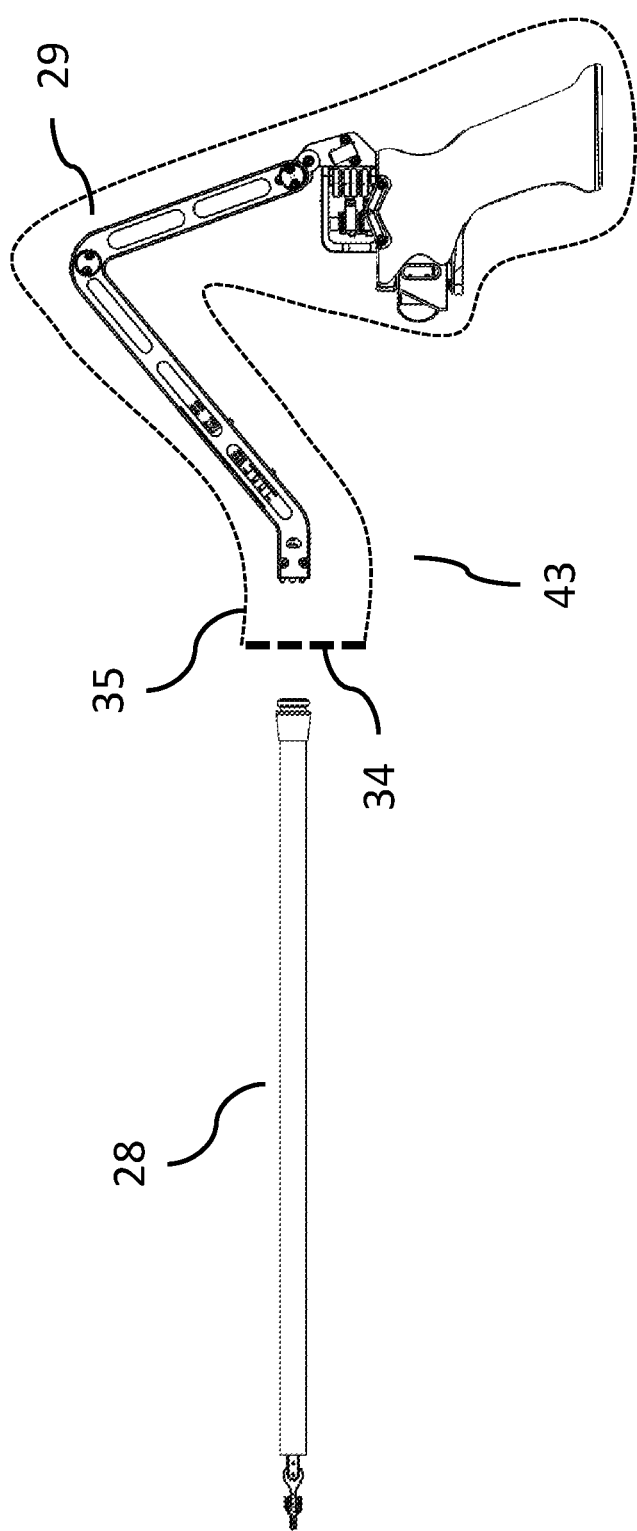
FIG. 25 shows schematically the sterile interface between the distal and proximal parts of the articulated instrument according to an embodiment of the current invention.

Since the distal part 28 of the surgical instrument 1 is partially entering the patient's body, it has to be sterile, just like the area in the vicinity of the patient. On the other hand, the proximal part 29 of the articulated instrument 1 may not be sterile and therefore should be separated from the sterile instrument portions 28 by a sterile interface 43 which protects the sterile area from the non-sterile components 29 of the articulated instrument 1 (FIG. 25).

The sterile interface 43 comprises two main components: a flexible sleeve 35, which covers the moving links of the proximal part 29 of the articulated instrument 1 and a rigid connector 35, which i) guarantees that the sterile distal part 28 of the articulated instrument 1 is not directly touching the non-sterile components of the proximal part 29, ii) enables attachment/detachment between the distal 28 and the proximal 29 parts of the articulated instrument 1, and iii) ensures the connection/disconnection of the mechanical transmission systems that deliver motion to the end-effector links 6, 7, 8.

Figure 26:
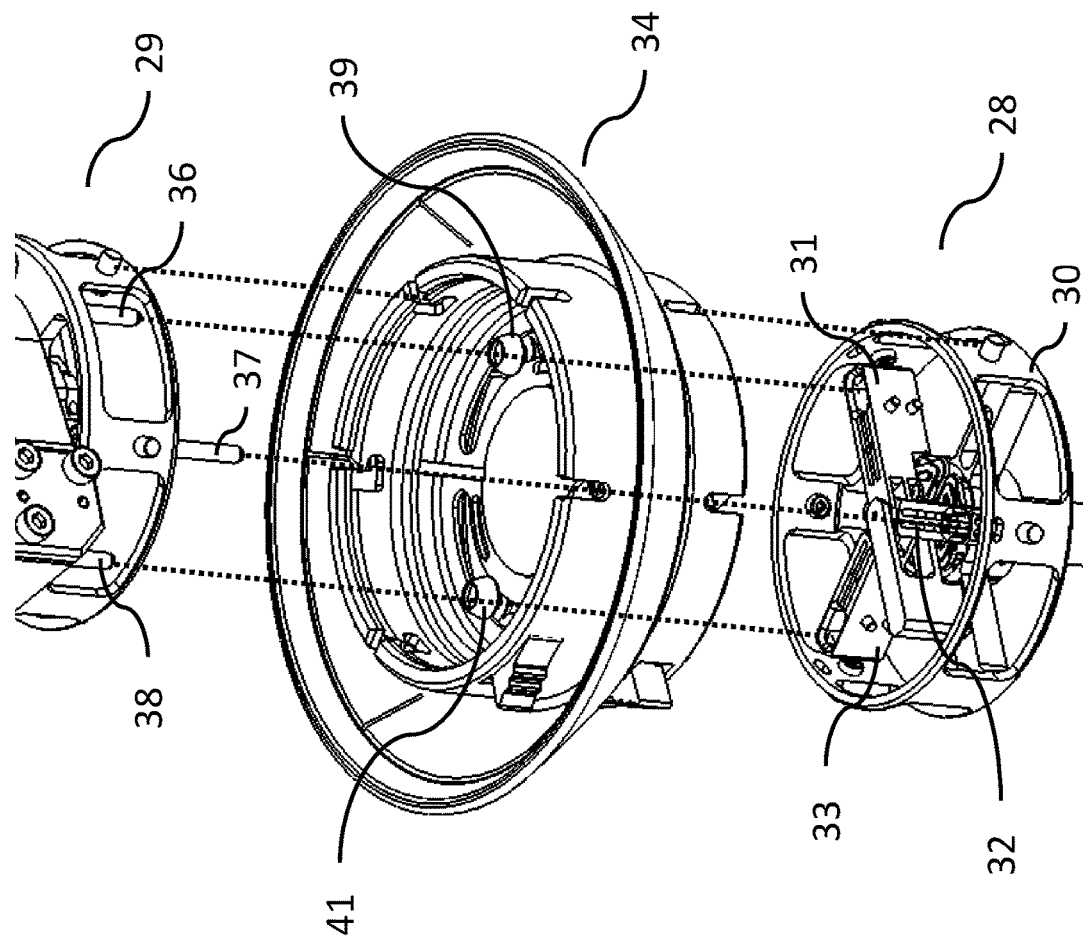
FIG. 26 shows a perspective view of a rigid connector composing a sterile interface operationally mounted between the distal and proximal parts of the articulated instrument according to an embodiment of the current invention.

FIG. 26 shows how the rigid connector 34 can be disposed and operationally mounted between the proximal hub 30 and the proximal part 29 of the articulated instrument 1. In order to connect/disconnect the mechanical transmission systems that deliver motion to the end-effector links 6, 7, 8, three cylindrical elements 36, 37, 38, from the proximal part 29 of the articulated instrument 1, are inserted on three miniature cups 39, 40, 41 of the rigid connector 34, which are then inserted on the rotating elements 31, 32, 33. In this way, it can be guaranteed that the sterile surgical instrument 28 is not directly touching non-sterile components.

In other embodiments of the current invention, the movement of some of the three cylindrical elements 36, 37, 38, from the proximal part 29 of the articulated instrument 1, may be constrained so that some degrees-of-freedom of the end-effector 2 can be locked/unlocked in their range of movement, allowing for instance the use of the articulated instrument 1 as a standard laparoscopic instrument, with a single degree-of-freedom at the end-effector.

The articulated hand-held medical instrument of the present invention is designed to be used in a full range of minimally invasive surgical procedures in combination with standard laparoscopic equipment. For example, the inventive instrument may optionally be inserted through a trocar and its movements inside the patient's body may be tracked with an available endoscopic camera. In addition, the articulated hand-held medical instrument may be used in a range of port arrangements in minimally invasive surgical procedures.

The articulated instrument 1 can assume other kinematics, like the kinematic models shown in FIGS. 28 to 31.

Figure 32:
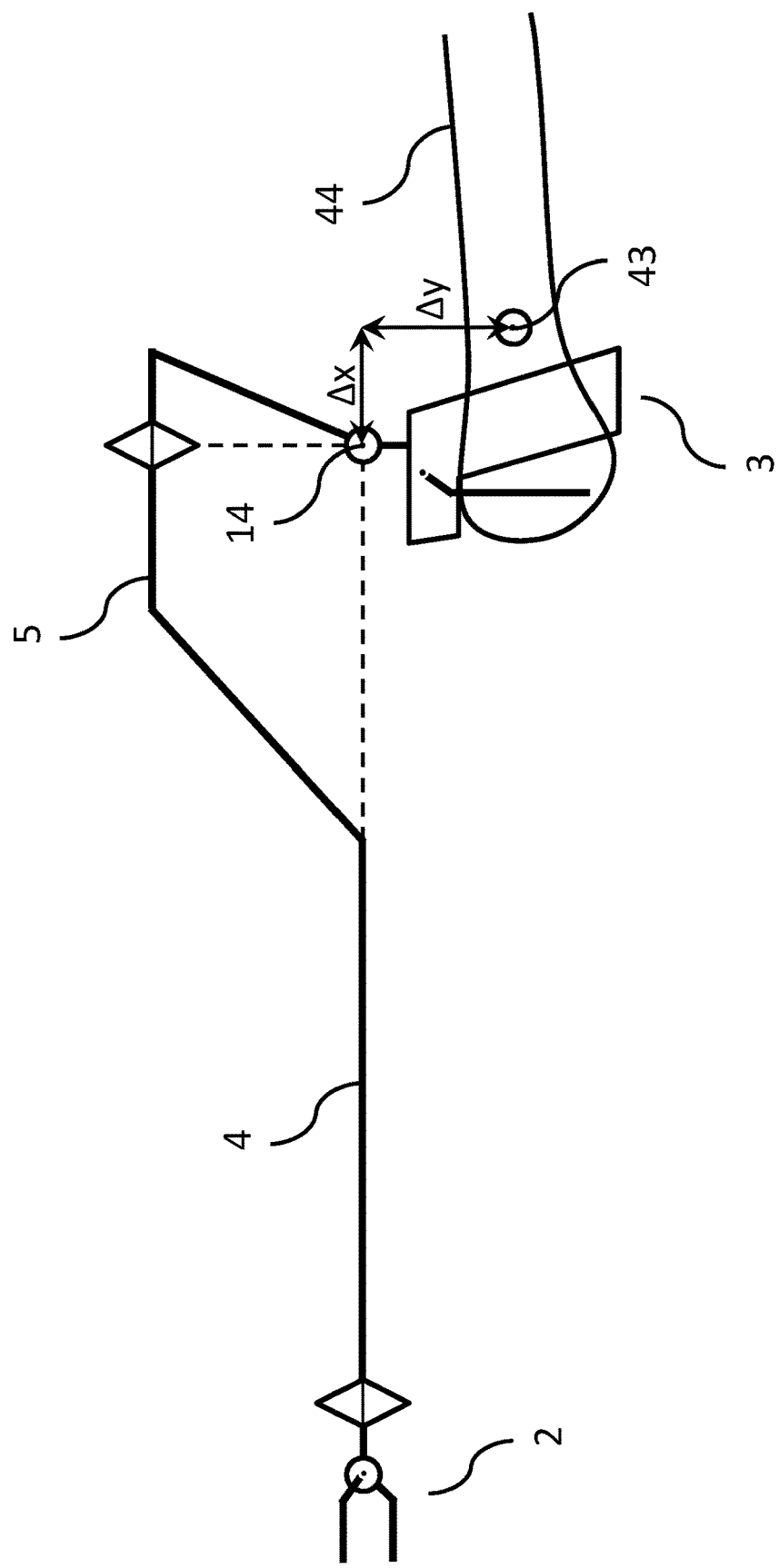
FIG. 32 shows a kinematic model of an embodiment of the present invention displaying the position of the user's wrist joint relative to that of a centre of rotation of the handle.
Figure 33:
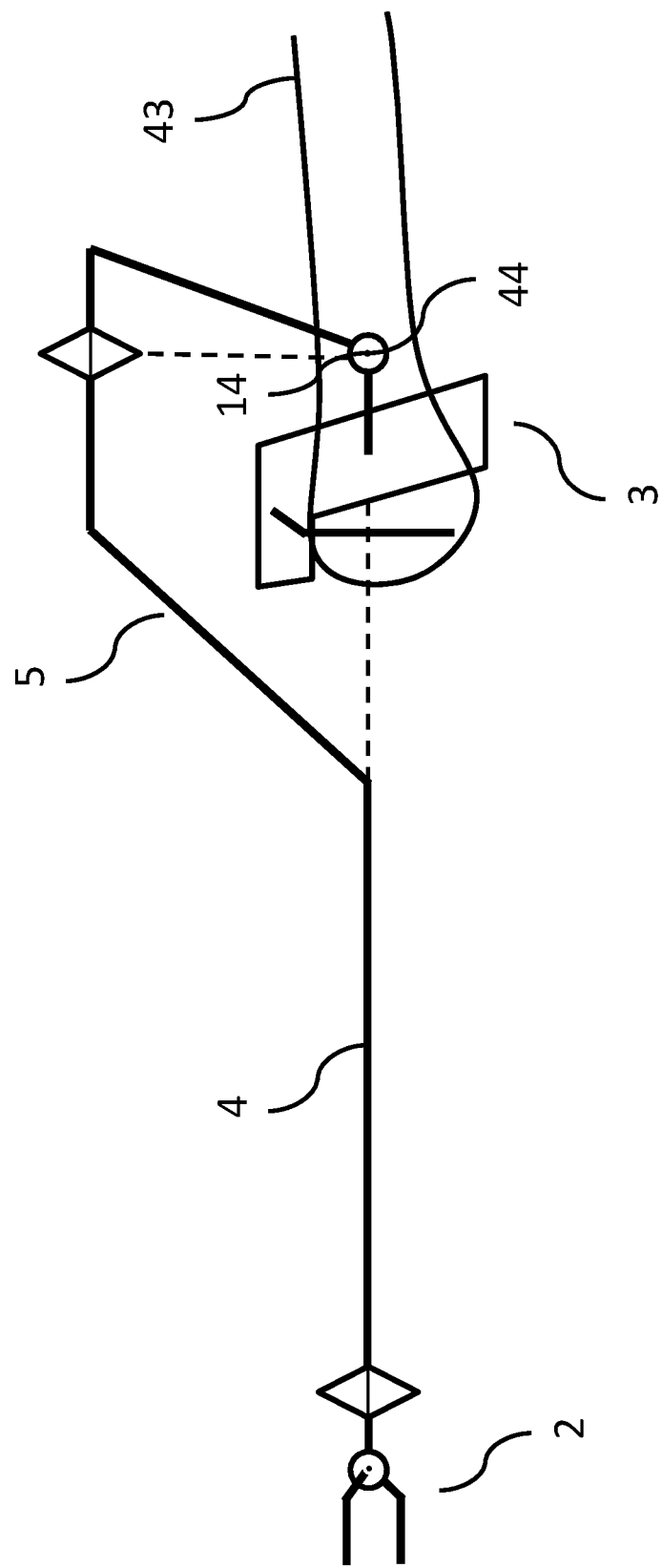
FIGS. 33 and 34 show alternative kinematic models of embodiments of the present invention displaying alignment of the user's wrist joint relative to the centre of rotation of the handle.
Figure 35:
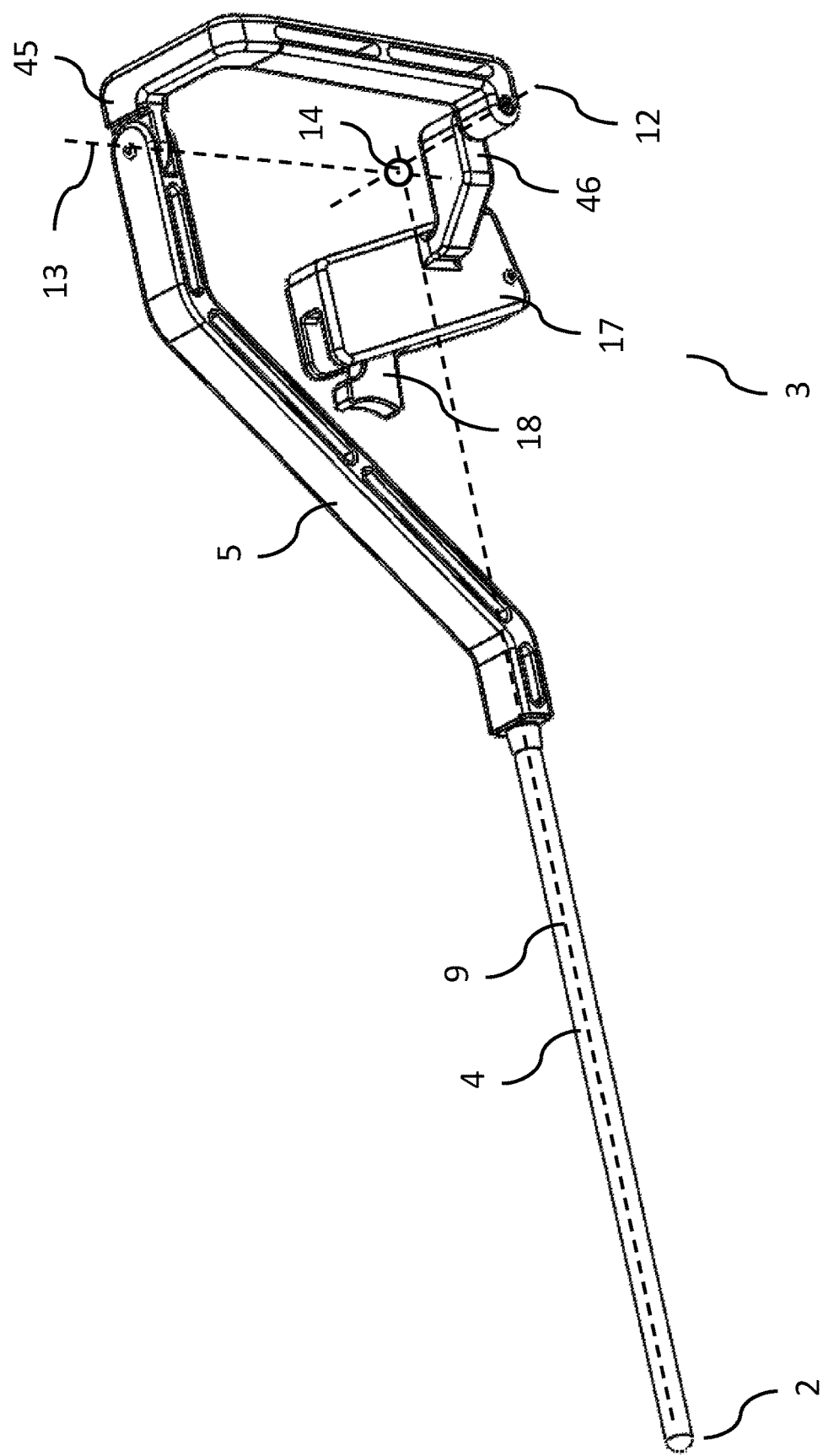
FIGS. 35, 36 and 37 show embodiments of the present invention where the user's wrist is in alignment with the centre of rotation of the handle.
Figure 36:
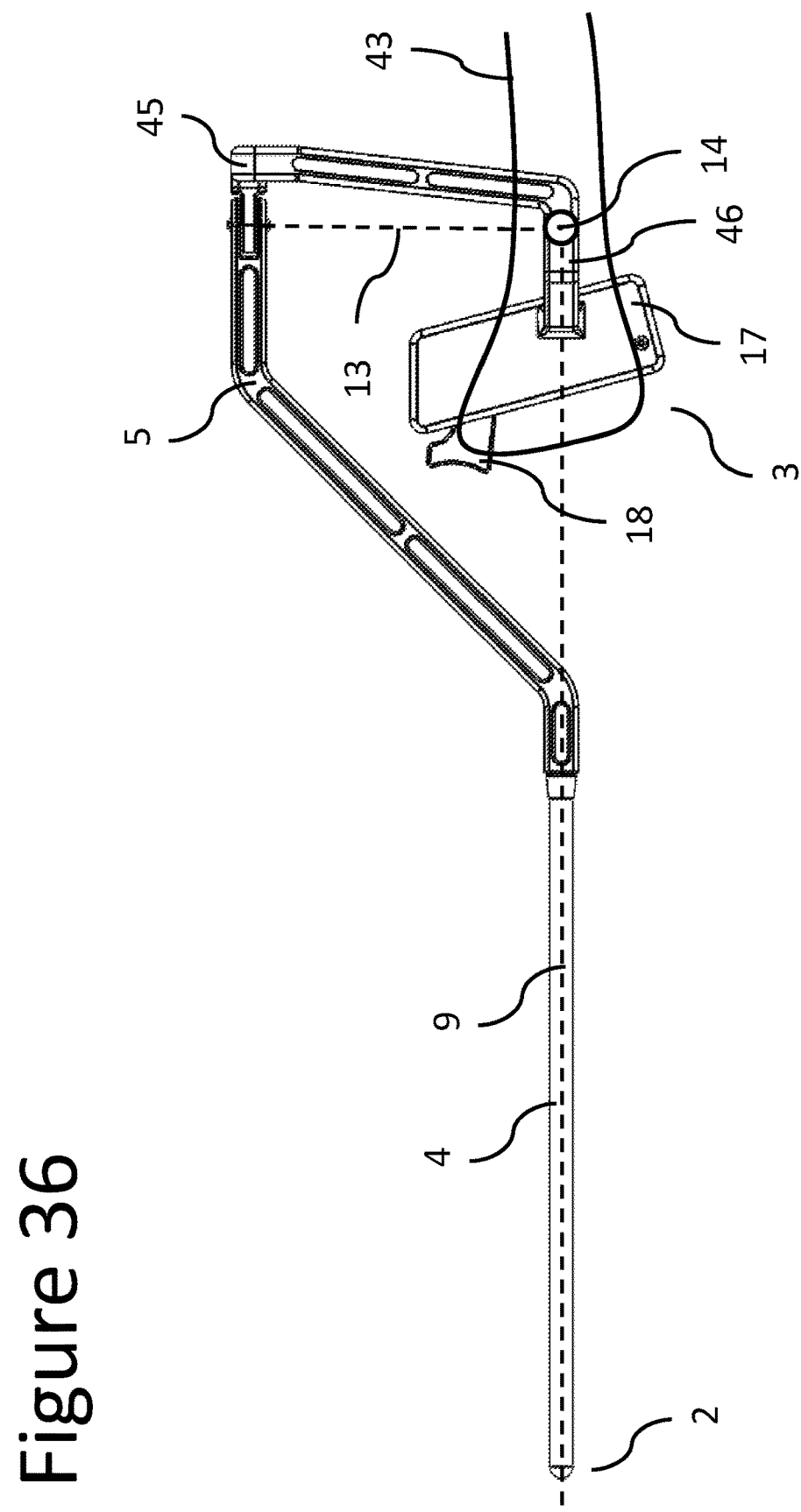
Figure 37:
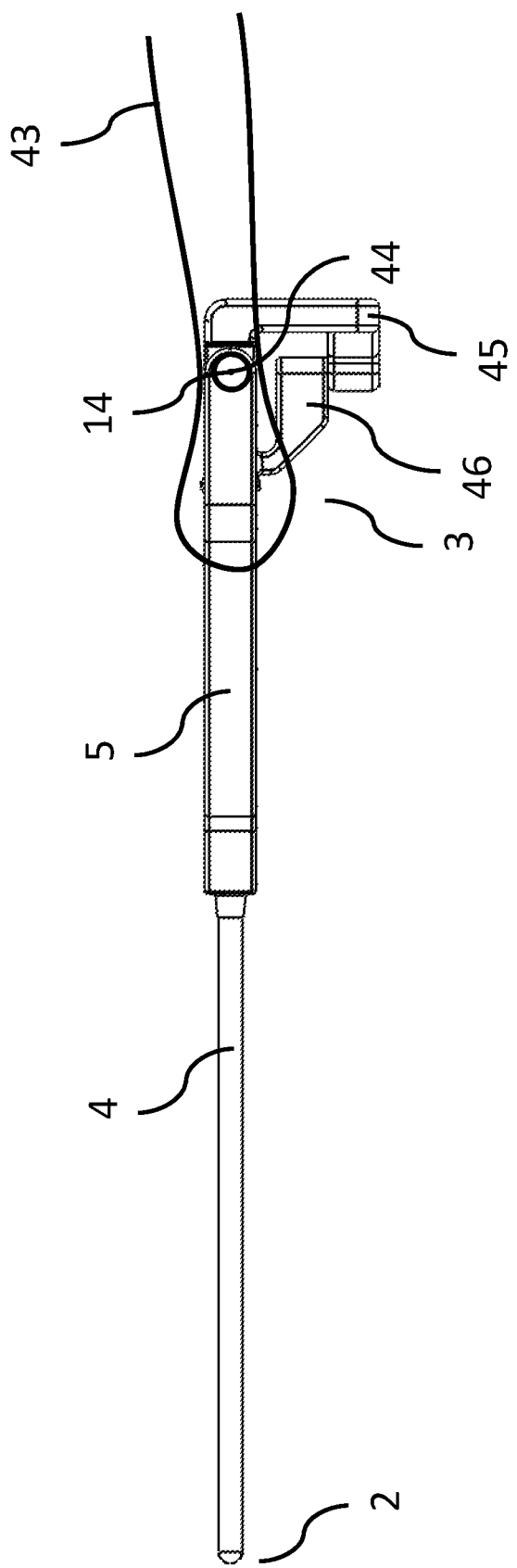

As illustrated in FIG. 32, in most of the embodiments (and kinematic models) described up to this point, the central rotation point 14 of the articulated handle 3 is not coincident with the central wrist point 43 of the user 44. However, these positional offsets $\Delta x$, $\Delta y$ (and possibly $\Delta z$) can create positional mismatches (also known as "parasitic movements") between the movements applied to the handle 3 and the movements generated at the end-effector 2. In particular, a pure rotation performed by the user's hand at the handle 3 might create a composed movement, of rotation plus a translation, of the end-effector 2. Therefore, in order to compensate for that, the central rotation point 14 and the central wrist point 43 have to be aligned. In order to achieve this, other kinematic models (like the ones of FIGS. 33, 38 and 39) can be used on the articulated instrument 1 of the current invention so that the central rotation point 14 is located in the free space and not within the structure of the moving links 5, 45, 46 (this kinematic feature may also be designated by Remote Center of Motion, RCM). In some of these embodiments, like the one of FIGS. 35, 36 and 37, there are three revolute joints whose axes 9, 12, 13 intersect at the RCM. Thus, the kinematics of the articulated instrument 1 can be set so that the central rotation point 14 (or RCM) is substantially coincident to the central wrist point 44 of the user 43. FIGS. 36 and 37 show a side and top view of this alignment.

Figure 38:
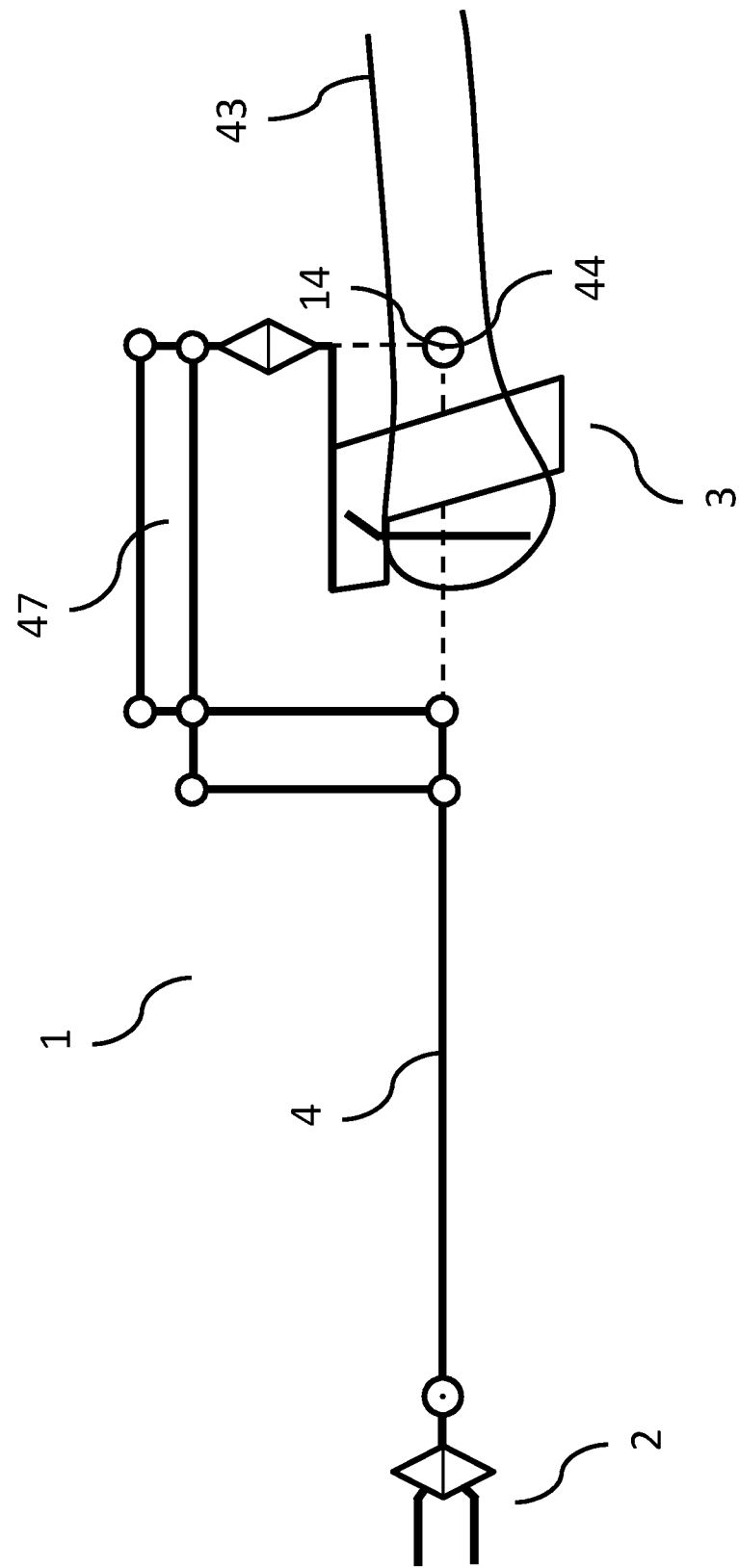
FIGS. 38 and 39 show kinematic models of embodiments of the present invention including a wrist alignment concept in accordance with the invention.
Figure 39:
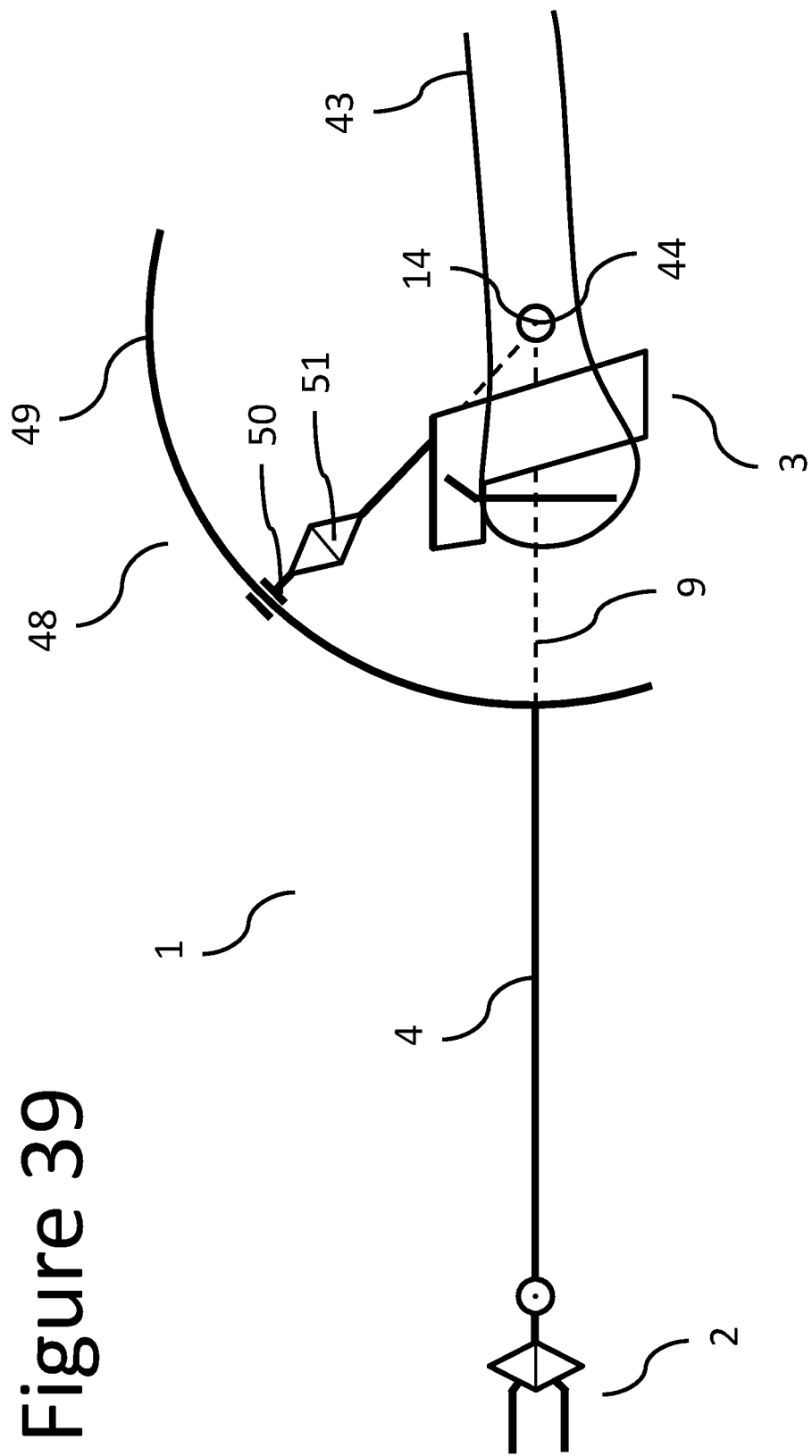

FIGS. 38 and 39 show two additional embodiments of the current invention using two different kinematic models. The articulated instrument 1 of FIG. 38 uses a double parallelogram mechanism 47 to achieve its RCM, where the central rotation point 14 is set to be substantially coincident to the central wrist point 44 of the user 43. The articulated instrument 1 of FIG. 39 uses a spherical mechanism, having a circular track 49 as the movement base, whose center is aligned with the axis 9 of the instrument shaft 4. Mounted on the circular track 49, a radial sliding element 50 comprises a collinear rotational joint 51 and is always aligned with the RCM (the central rotation point 14) at the center of the circular track 49.

Figure 41:
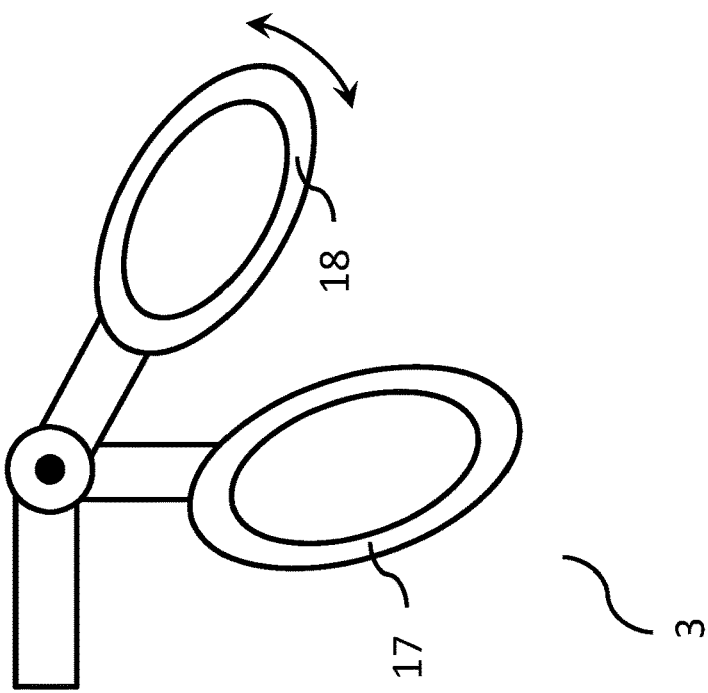
FIGS. 40 and 41 show representative handle links that may be used in accordance with embodiments of the present invention.
Figure 40:
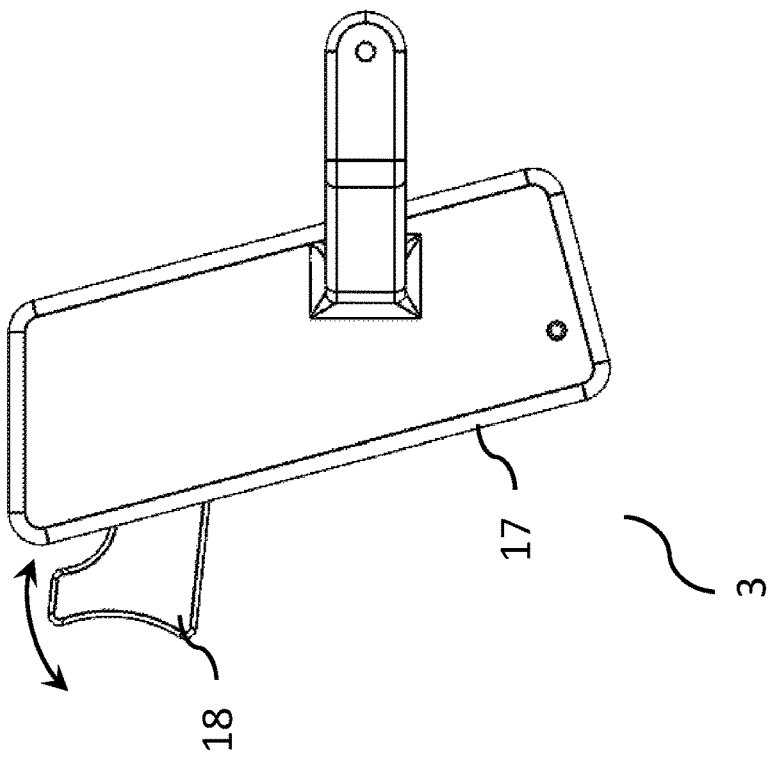

In order to provide an ergonomic manipulation and gripping functionality to the user, the handle 3 of the articulated instrument 1 may be compatible with handle links 17 and 18 of multiple shapes and sizes. Therefore, while in the embodiment of FIG. 40, the handle links 17 and 18 may have a joystick-like or pistol-grip-like shape, in the embodiment shown in FIG. 41, the handle links 17 and 18 have a scissors-like or needle-holder-like configuration.

Figure 34:
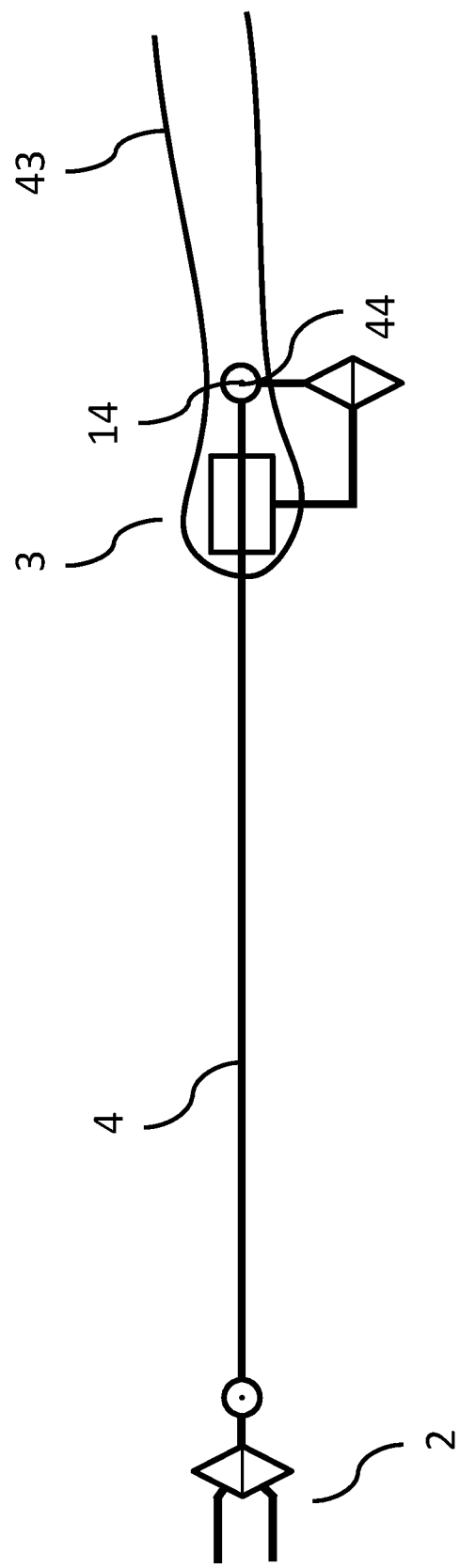
Figure 44:
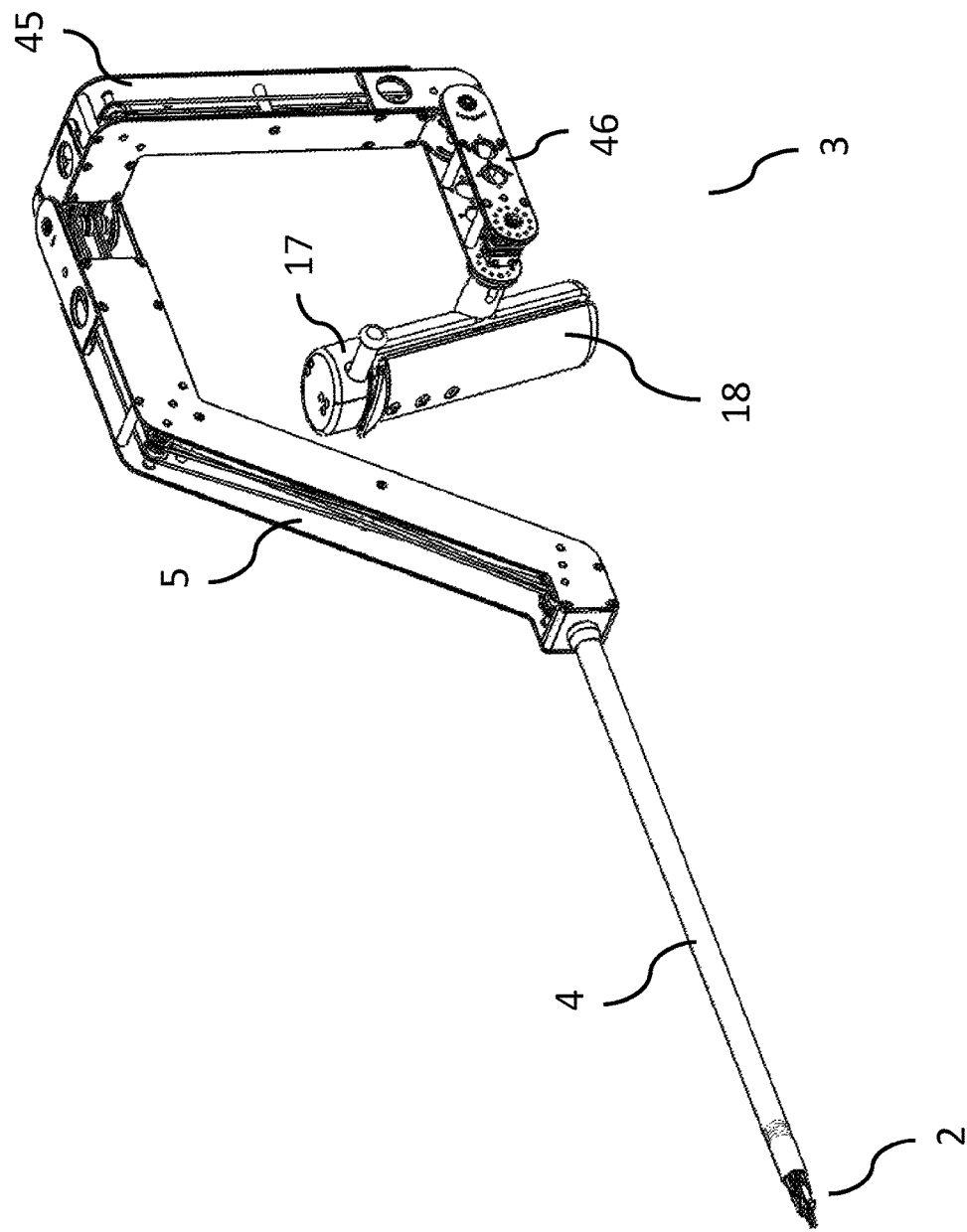
FIGS. 44, 45 and 46 show different views, with main dimensions, of a detailed design of an embodiment of the present invention.
Figure 45:
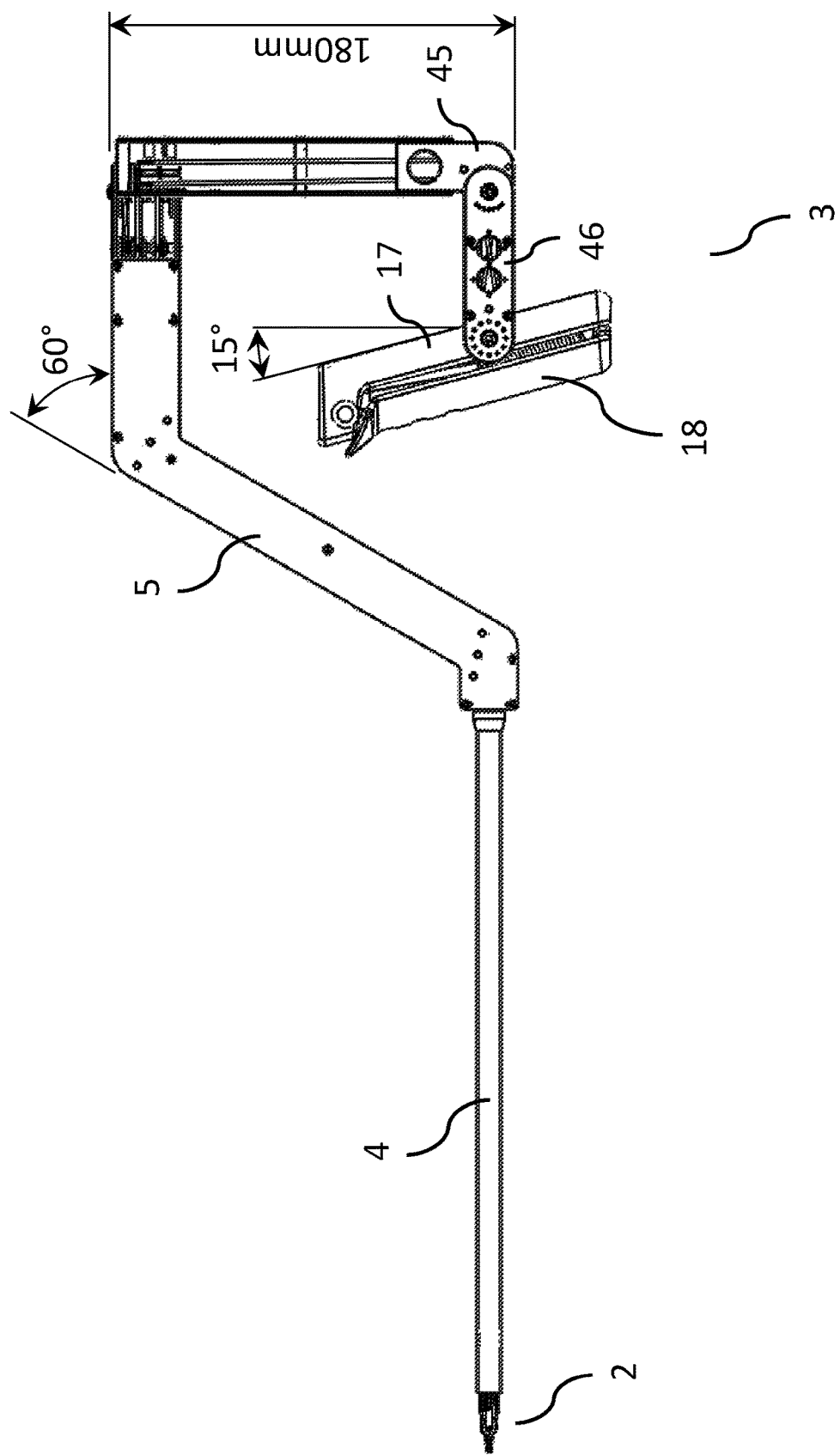
Figure 46:
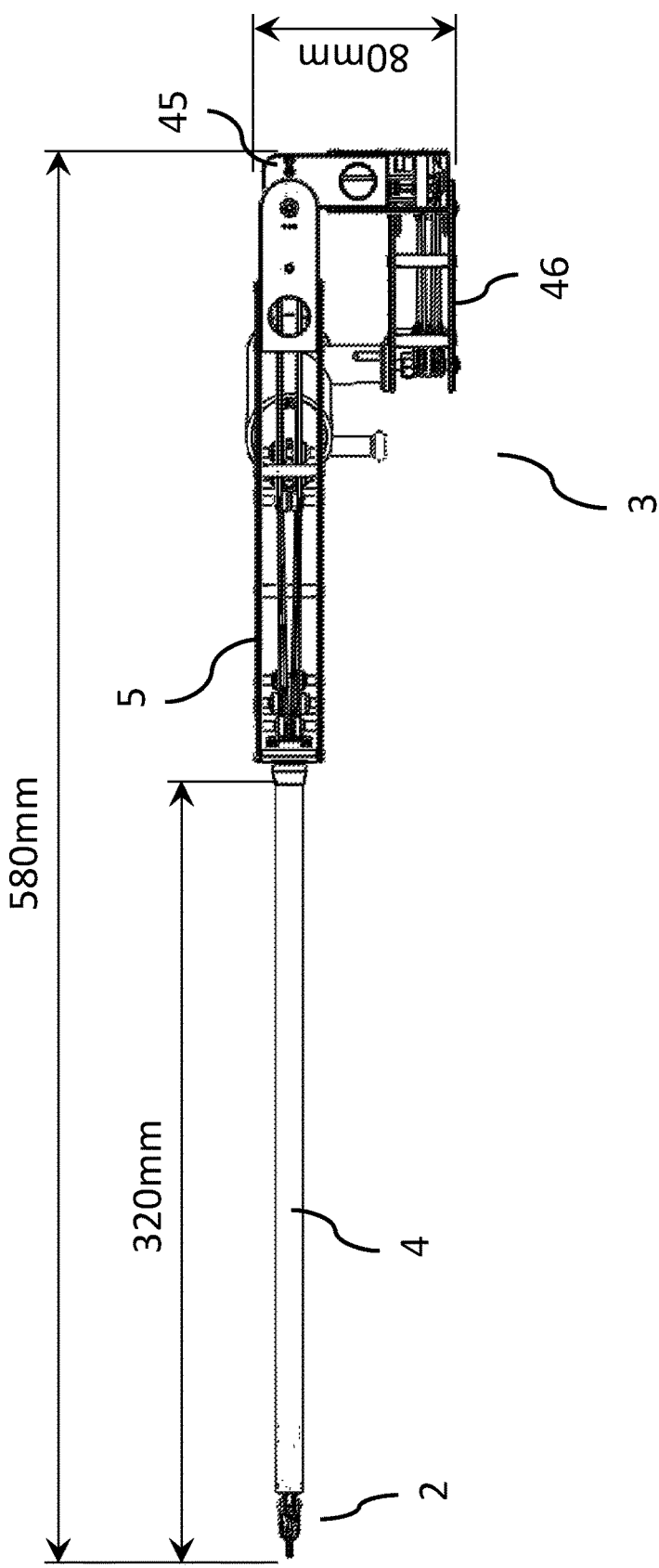

FIGS. 44 to 46 show three different views (with main dimensions) of a possible embodiment of the current invention. These figures show a detailed design version of the embodiment of FIGS. 35 to 37, with the kinematic model of FIGS. 33 and 34.

In order to be as light in weight as possible, the articulated instrument 1 may be, in the main, constructed of aluminum components, although the invasive part of the instrument should be mainly constructed of medical grade stainless steel and polymers. The mechanical transmission is essentially constructed of tungsten ropes, although steel or polymeric ropes could also be used in some specific situations, depending on the target number of cleaning and sterilization cycles that the instrument should support.

Figure 47:
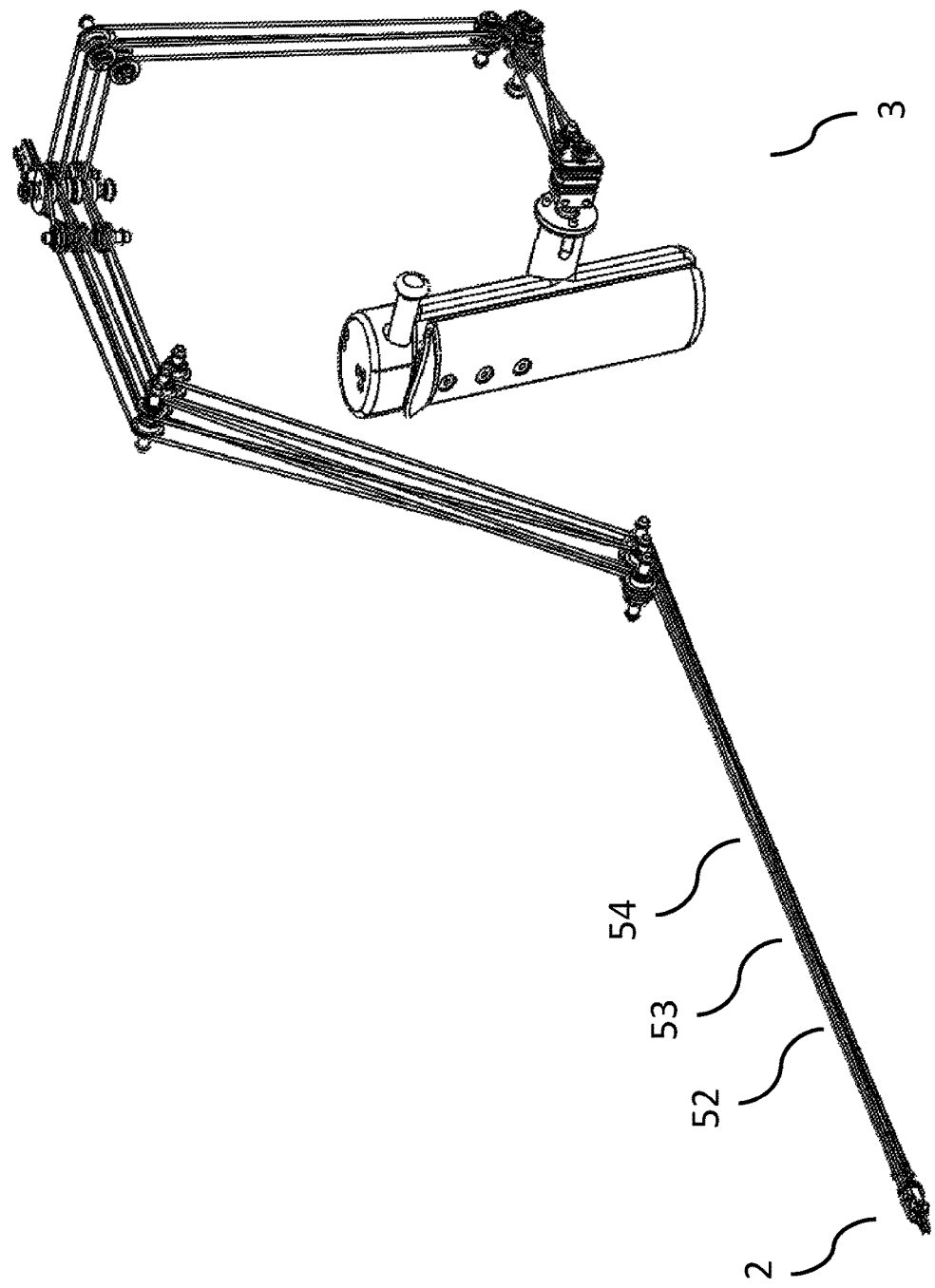
FIGS. 47, 48 and 49 show the mechanical transmission elements of the different degrees-of-freedom of the instrument, in accordance with various embodiments of the present invention.
Figure 48:
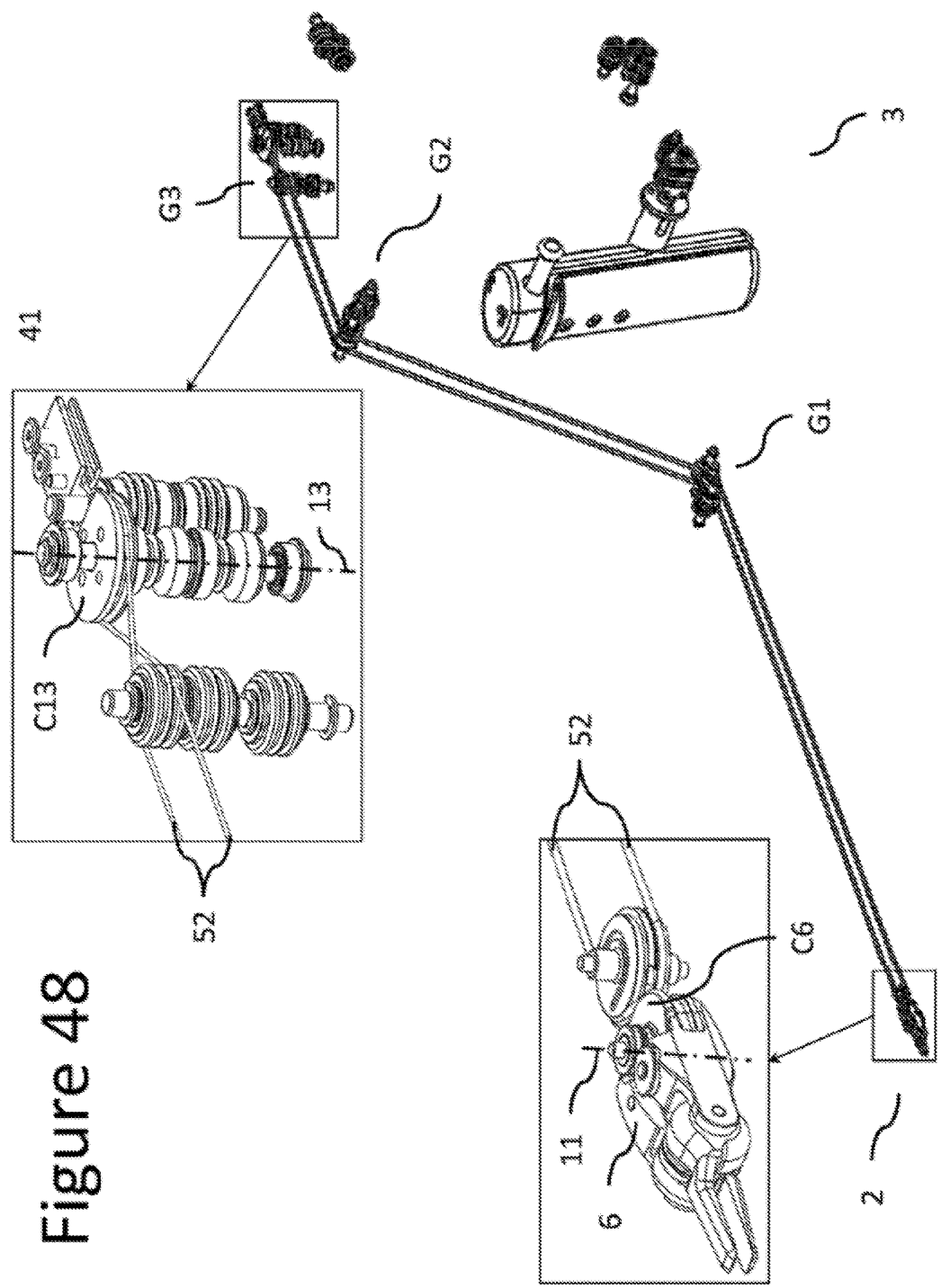
Figure 49:
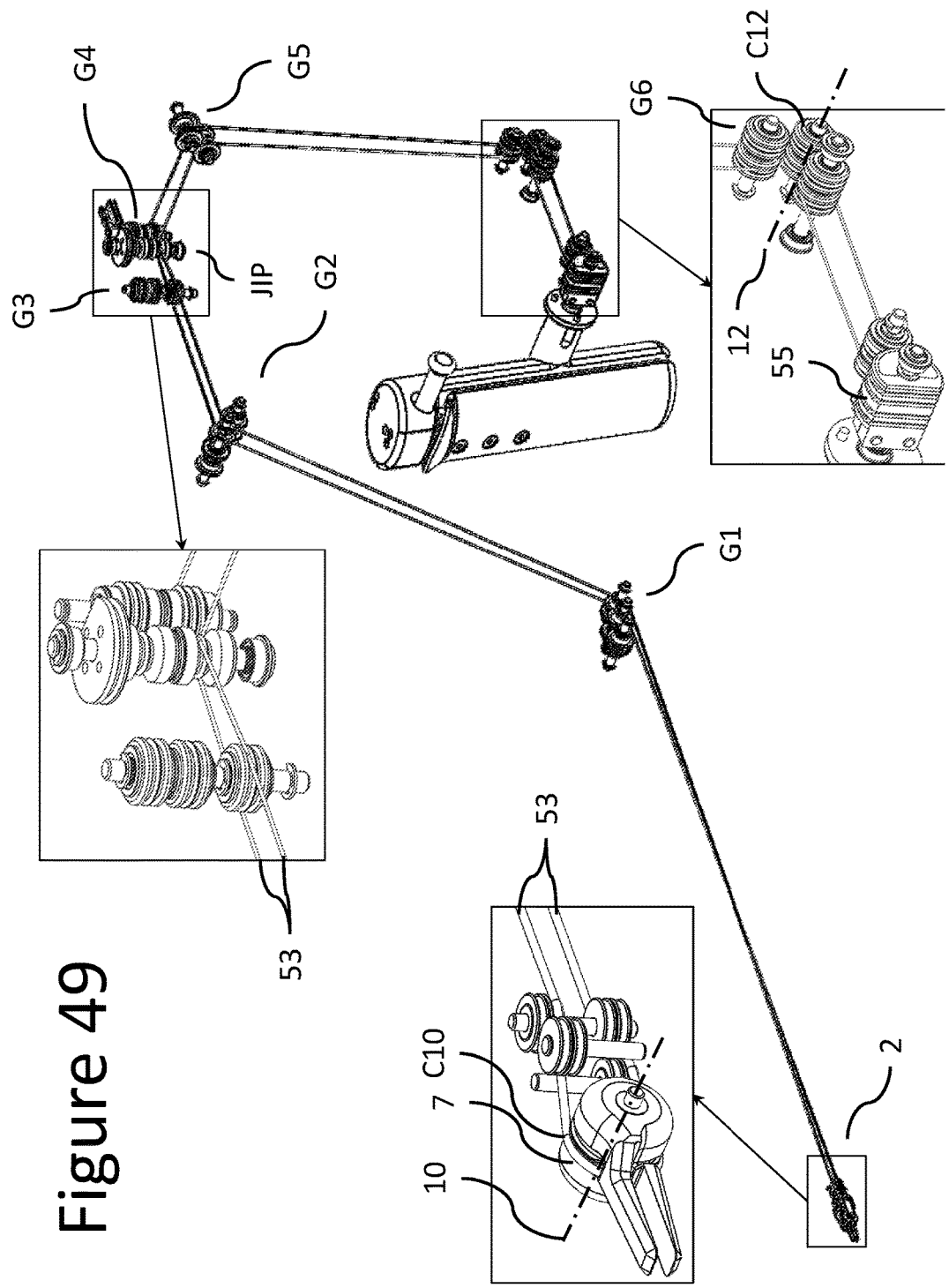

The mechanical transmission elements for each one of the three degrees of freedom of the instrument are shown are shown in FIG. 47 to FIG. 49, as described in more detail below.

FIG. 48 shows the transmission of motion between the handle 3 and end-effector 2 for the proximal degree of freedom. Joints around the axes 11 and 13 are connected by a cable 52 in a single closed loop configuration (in some embodiments, it may comprise two segments of cable 52*a* and 52*b*) which runs from a driving pulley C13 connected to the proximal handle link 45 and passing through 3 sets of guiding pulleys G1, G2 and G3 up to a driven pulley C6, connected to the proximal end-effector link 6. The sets of guiding pulleys are used to shape the path of the transmission cables to the geometry of the frame 5 or handle links.

FIG. 49 shows the transmission of motion between the handle 3 and end-effector 2 for a first distal degree of freedom. Joints around the axes 10 and 12 are connected by a cable 53 in a single closed loop configuration (in some embodiments, it may comprise two segments of cable 53*a* and 53*b*) which runs from a driving pulley C12 up to a driven pulley C10, connected to the proximal end-effector link 7. On their path from the driving pulley C12 to the driven pulley C6, the closed loop cable 53 passes through 6 sets of guiding pulleys G1, G2, G3, G4, G5, G6 and a set of joint idle pulleys JIP. Although this degree-of-freedom is driven by pulley C12, the closed cable loop is not directly attached to it. Instead they are attached to a distal actuation pulley 55, which couples the movement of the two distal degrees-of-freedom (shown in FIGS. 8 and 9) so that they perform the actuation of the instrument in parallel. The motion transmission between the handle 3 and end-effector 2 for the second distal degree of freedom is analogous, with a similar arrangement of cable loops and pulleys.

Figure 50:
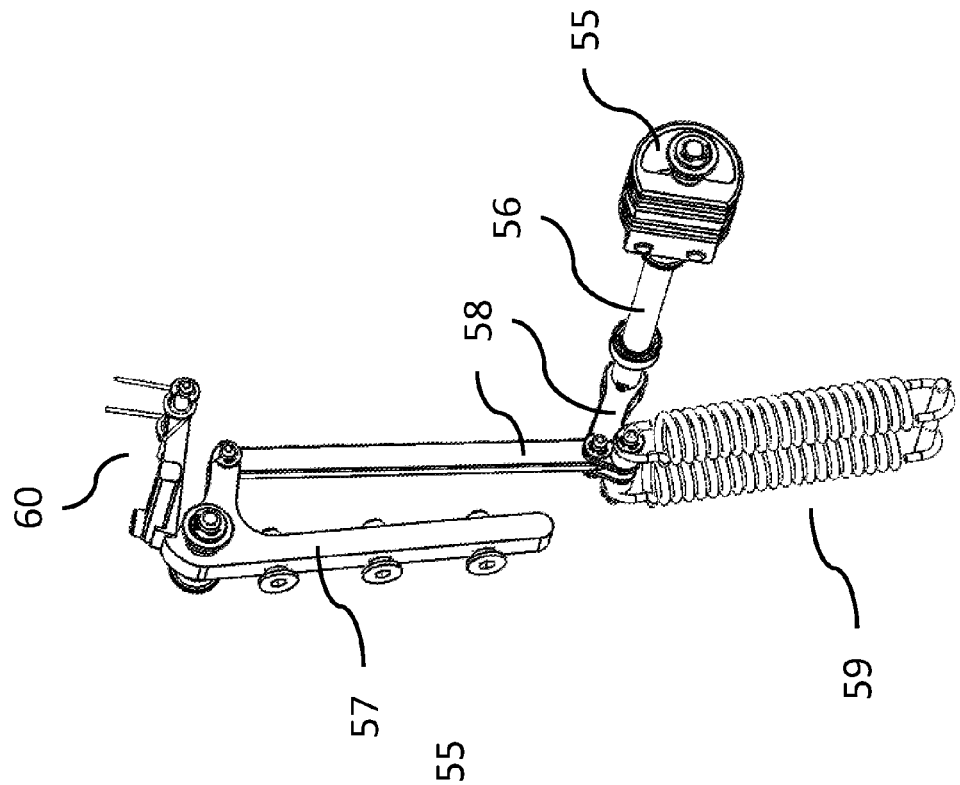
FIGS. 50 and 51 show detailed views of the instrument's actuation system, in accordance with various embodiments of the present invention.
Figure 51:
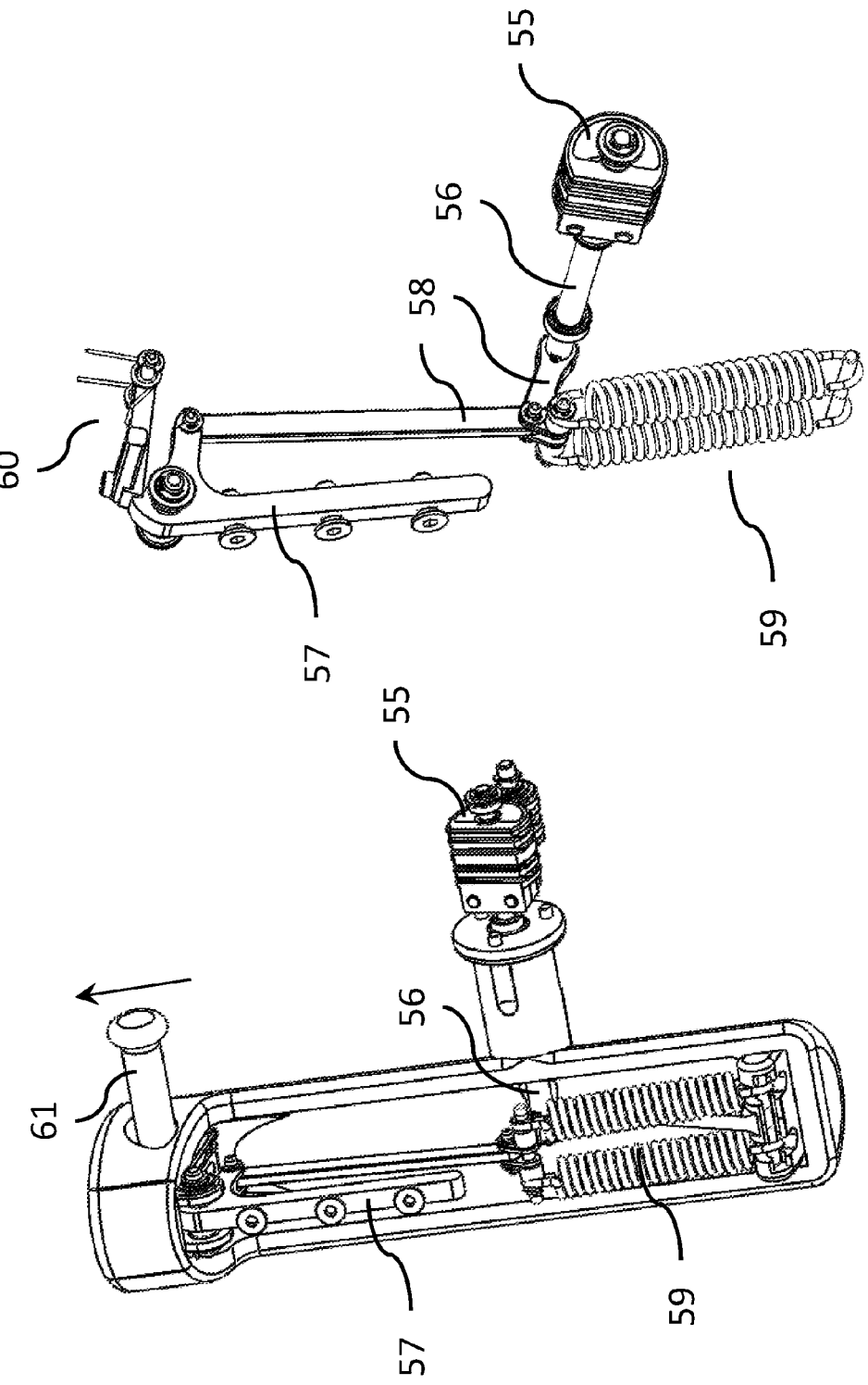

Attached to the distal actuation pulley 55, there is an actuation shaft 56 (FIGS. 50 and 51), which transmits the actuation input movement from the handle link 18. Handle link 18 is rigidly attached to an actuation link 57, which is connected by a linkage system 58 to the actuation shaft 56. A spring system 59 is permanently acting on the linkage system 58, bringing the actuation link 57 to a default open position. When brought to its maximum closed position, the actuation link 57 can be temporarily blocked by a spring-actuated ratcheting mechanism 60, which can be deactivated by pressing up the thumb trigger 61.

While this invention has been shown and described with reference to particular embodiments thereof, it will be understood by those skilled in the art that various changes in form and details may be made therein without departing from the spirit and scope of the invention as defined by the appended claims.

The invention claimed is:

1. A handheld surgical instrument comprising:
   an instrument shaft having a proximal end and a distal end;
   an articulated handle;
   an articulated end effector connected to the distal end of the instrument shaft;
   a structural frame having a proximal end mounted on the articulated handle and a distal end coupled to the proximal end of the instrument shaft, the structural frame comprising three joints, each of the three joints having an axis that intersects at a remote center of motion of the handheld surgical instrument, the remote center of motion configured to be coincident to a central point of a user's wrist; and
   a flexible mechanical transmission system connecting the articulated handle to the articulated end effector such that motion applied to the articulated handle is reproduced at the articulated end effector,
   wherein the articulated end effector comprises at least three orientation or actuation degrees of freedom, and
   wherein the flexible mechanical transmission system follows a continuous path from a proximal end of the articulated handle to the distal end of the articulated handle and then from the proximal to the distal end of the structural frame and then from the proximal to the distal end of the instrument shaft and then from a proximal end of the articulated end-effector to a distal end of the articulated end effector.

2. The handheld surgical instrument of claim 1, wherein the flexible mechanical transmission system comprises a system of cables and pulleys disposed at the articulated handle and articulated end effector.

3. The handheld surgical instrument of claim 2, wherein the flexible mechanical transmission system comprises a closed loop configuration.

4. The handheld surgical instrument of claim 3, wherein at least one of the cables of the system of cables and pulleys runs from a driving pulley coupled to the articulated handle, through a plurality of guiding pulleys, to a driven pulley coupled to the articulated end effector.

5. The handheld surgical instrument of claim 1, wherein the handle comprises a joystick-like or pistol-grip-like shape.

6. The handheld surgical instrument of claim 1, wherein a geometry of the structural frame allows alignment of the human user's wrist with the remote center of motion of the handheld surgical instrument.

7. The handheld surgical instrument of claim 6, wherein the geometry of the structural frame allows the articulated handle a full range of movement without colliding with the instrument shaft.

8. The handheld surgical instrument of claim 1, wherein the articulated handle comprises a plurality of handle links connected by a corresponding plurality of handle joints and wherein the articulated end effector comprises a plurality of end-effector links connected by a corresponding plurality of end effector joints, and wherein the number of handle links is equal to the number of end-effector links.

9. The handheld surgical instrument of claim 1, wherein the handle comprises a scissors-like or needle-holder-like configuration.

10. The handheld surgical instrument of claim 1, wherein the at least three degrees of freedom of the articulated end effector comprise at least two orientational degrees of freedom and at least one actuation degree of freedom.

11. The handheld surgical instrument of claim 10, wherein at least two of the orientational degrees of freedom have a serial kinematic disposition.

12. The handheld surgical instrument of claim 10, wherein the at least one actuation degree of freedom is disposed in parallel to the orientational degrees of freedom.

13. The handheld surgical instrument of claim 1, wherein the flexible mechanical transmission system comprises cables made from steel or tungsten.

14. A method for performing a minimally invasive, remotely actuated surgical procedure using the handheld surgical instrument of claim 1, the method comprising:
   positioning the user's hand at the articulated handle such that the remote center of motion of the handheld surgical instrument is coincident with the central point of the user's wrist;
   laparoscopically introducing the articulated end effector into a patient to a desired location for the surgical procedure; and
   actuating the articulated handle such that motion applied to the articulated handle is reproduced at the articulated end effector in at least one orientation or actuation degrees of freedom via the flexible mechanical transmission system for performing the surgical procedure.

15. The method of claim 14, wherein the motion reproduced at the articulated end effector comprises a composed movement of rotation and translation.

16. The method of claim 14, wherein the at least one orientation or actuation degrees of freedom comprises at least two orientational degrees of freedom and at least one actuation degree of freedom.

17. The method of claim 14, wherein a geometry of the structural frame allows the user to articulate the articulated handle in a full range of movement without colliding with the instrument shaft.

18. A handheld surgical instrument comprising:
   an instrument shaft having a proximal end and a distal end;
   an articulated handle;
   an articulated end effector connected to the distal end of the instrument shaft;
   a structural frame having a proximal end mounted on the articulated handle and a distal end coupled to the proximal end of the instrument shaft, the structural frame comprising three joints, each of the three joints having an axis that intersects at a remote center of motion of the handheld surgical instrument, the remote center of motion configured to be coincident to a central point of a user's wrist; and
   a flexible mechanical transmission system connecting the articulated handle to the articulated end effector such that motion applied to the articulated handle is reproduced at the articulated end effector,
   wherein the articulated end effector comprises at least three orientation or actuation degrees of freedom, and
   wherein the articulated handle comprises a plurality of handle links connected by a corresponding plurality of handle joints and wherein the articulated end effector comprises a plurality of end-effector links connected by a corresponding plurality of end effector joints, and wherein the number of handle links is equal to the number of end-effector links.

19. The handheld surgical instrument of claim 18, wherein motion applied to a particular handle link is reproduced at the corresponding end-effector link.

20. A handheld surgical instrument comprising:
an instrument shaft having a proximal end and a distal end;
an articulated handle;
an articulated end effector connected to the distal end of the instrument shaft;
a structural frame having a proximal end mounted on the articulated handle and a distal end coupled to the proximal end of the instrument shaft, the structural frame comprising three joints, each of the three joints having an axis that intersects at a remote center of motion of the handheld surgical instrument, the remote center of motion configured to be coincident to a central point of a user's wrist; and
a flexible mechanical transmission system connecting the articulated handle to the articulated end effector such that motion applied to the articulated handle is reproduced at the articulated end effector,
wherein the articulated end effector comprises at least three orientation or actuation degrees of freedom,
wherein the flexible mechanical transmission system comprises a system of cables and pulleys disposed at the articulated handle and articulated end effector and the flexible mechanical transmission system comprises a closed loop configuration, and
wherein at least one of the cables of the system of cables and pulleys runs from a driving pulley coupled to the articulated handle, through a plurality of guiding pulleys, to a driven pulley coupled to the articulated end effector.

* * * * *